(12) United States Patent
Wiig et al.

(10) Patent No.: US 8,546,647 B2
(45) Date of Patent: Oct. 1, 2013

(54) PATHOGEN INDUCIBLE PLANT THEHALOSE-6-PHOPHATE PHOPHATASE GENE PROMOTERS AND REGULATORY ELEMENTS

(75) Inventors: Aaron Wiig, Chapel Hill, NC (US); Robert Ascenzi, Cary, NC (US); Xiang Huang, Apex, NC (US); Sumita Chaudhuri, Cary, NC (US); Rui-Guang Zhen, Chapel Hill, NC (US); Yu Han, Cary, NC (US)

(73) Assignee: BASF Plant Science GmbH (DE)

( * ) Notice: Subject to any disclaimer, the term of this patent is extended or adjusted under 35 U.S.C. 154(b) by 671 days.

(21) Appl. No.: 12/518,676

(22) PCT Filed: Dec. 12, 2007

(86) PCT No.: PCT/EP2007/063761
§ 371 (c)(1),
(2), (4) Date: Jun. 11, 2009

(87) PCT Pub. No.: WO2008/071726
PCT Pub. Date: Jun. 19, 2008

(65) Prior Publication Data
US 2009/0271891 A1    Oct. 29, 2009

Related U.S. Application Data

(60) Provisional application No. 60/874,375, filed on Dec. 12, 2006.

(51) Int. Cl.
*C12N 15/82* (2006.01)
*C12N 15/63* (2006.01)
*C12N 15/87* (2006.01)

(52) U.S. Cl.
USPC ............... 800/287; 435/320.1; 536/24.1

(58) Field of Classification Search
USPC .............................................. 800/287
See application file for complete search history.

(56) References Cited

U.S. PATENT DOCUMENTS
7,439,348 B2 * 10/2008 Diehn et al. ............... 536/24.1

FOREIGN PATENT DOCUMENTS
WO    WO 99/45129    9/1999
WO    WO 03/033651    4/2003

OTHER PUBLICATIONS

Lin et al. 2001, Genbank accession: AC027032.*
Tair Annotation of locus AT1G35910, 2010.*
Godelieve Gheysen, et al, "The Exploitation of Nematode—Responsive Plant Genes in Novel Nematode Control Methods" Pestic. Sci. 1996, 47, 95-101, Great Britain.

* cited by examiner

*Primary Examiner* — Li Zheng
(74) *Attorney, Agent, or Firm* — Patricia A. McDaniels

(57) ABSTRACT

The invention provides plant gene promoters and regulatory elements that are root-specific and/or induced by parasitic nematodes. The promoters of the invention are useful for controlling expression of nucleic acids of interest in plants' roots. The invention also provides expression cassettes including the plant gene promoters and regulatory elements of the invention, transgenic plants containing such expression cassettes, and methods of producing such transgenic plants.

7 Claims, 21 Drawing Sheets

Figure 1

SEQ ID NO:1

```
   1 GTAGTGCCCT TCATGGATAC CAAAAGAGAA AATTTGATTT AGTGCATACA
  51 TATAACAATA TAACGCCGCA TAATAATACT GTATAAAACA GTCATGTAAC
 101 GATATGACAG CAGTAATACA GTTCCAAGAG ACGTTATAAT CGTATGCAAT
 151 CATATGCTTG CGTAGATTTT CCAACAGTTT TGTTTCGTTG ATAGGAGGAA
 201 CTCAACACTC TAGGGTAGTG ATTGGTAGAC ACTATTAGCA CAAAAAATAT
 251 TAATTTTACT CTGATGTTTA CCAAAAAAGT TACCAATCAA ATATTTAAGA
 301 GATCGTACTC TTCCACGGCG ACTCTAAAAA CCAAAGATAT AGGTTAGACT
 351 CATAACTACT TTATAAAGAA AATGTTTAAC GATAACTACC GAGATCTAAT
 401 AAATAAACCT TCATTTTCAA GTATATTATA TTTGCTTCTT TTGTTTATAT
 451 ATCAAACCAA GTTCTGGTTT ATAAAAATAT TAGATAAAAC TCGTCTAAAT
 501 AGGTAGGTGT AAAATAAAAT TTTAAATTTT TATCGATAAT ATTTAAAATT
 551 TGAAAAGTTA ATAATGATCC ACACATTTTT TCTAATATTT AATTTAGTAA
 601 TTTTTGTATT AAATAAAATT TCAATCATAT ACATTCGATT TTTCTATACA
 651 TTTTAACTAT CTATTTCTGC ATAATAAACT GTATTTTCAT TTTATACGCT
 701 TCATCTTATG GATGATATTT AAATTTTAAA TAGTAATTCA TACACTTTTT
 751 AATATTTAAT TTAGTATTTT CTTAAATCCA AATTTTAATC TTACAATTTA
 801 AATATCTACT TTAACATAAT ACAAATACAA TTTAATTTCA TTGTATTAAA
 851 TTCAAATATA ATTTGATTAT AATAAAATAC AATTTAATTC TAAAAGTCC
 901 ATCTTAGATT TTAATTTTCC TTTTTAGTTT TGAAAATTAA AAATTTAAAT
 951 TTATTAGATA TATATGTTAC TTTTTCAGTT TTCCTATTTA TTTAAGAAAA
1001 AAATATTTTT TAACACATGT CAACTTGTAA ACAATAGACT GAACACGTCA
1051 TTTTATATTA TGTTTAGTTT TGAAAATTAA AGTTAATTAA ATATTTATAT
1101 TTCTTTTTTT TAGCTTTTCT AATTATTTTT AAAATAGTAA ATATTTTTAA
1151 TACAAATCAA TATCTGAACA ATAGATTTGA TACATAACAT AATCCTATAA
1201 ATTATTAACT TGGAAAACGA TAGTTTATAT AATAAAATTA TTTTCTTAAG
1251 TTCTCTAACC ATAACAATTA AACTATATTT TAGCGAAGAA AAGAAGAGAA
1301 TACCGAGAGA ACGCAACTTG CACTAAAAGC TACCACTTTG GCAAATCACT
1351 CATTTATATT ATTATATACT ATCACCTCAA TTCAATCGAA ACCTCAAAAT
1401 AACACTAATA TATACACAAA GAAACAACAG AATAACACCG AAGAATATAG
1451 GTTTAGGAAA ATCCAGAATT TGTTGAGACT AAAGAGATCA AATTTTCGAT
1501 ACAAGGTTTT GCTCAATTTG TATTTCATA ATAAAATTCT TTATTTCACC
1551 ATAGACTTAC ATGATTAGTT TTCTTTTAA TAAAAAAAA CACGCGACAT
1601 GAAAATTATA TTATCTCAGT GTTGTCGAAT TTGAATTTGA ATTTTGAGTT
1651 AAATACTACA CATTTGTTGA CAACTTATTA AACTTTACAA GTCTGCTAC̲A̲
1701 ̲AATATTGTCA̲ ̲AATATTTACT̲ ̲AATTAATGGA̲ ̲CCAAATCCT̲ ̲CTAACTTGCA̲
1751 ̲AATTTGTATC̲ TACATCAACT TAAAAATTAG GAATATGCGA CCCAAAAAAA
1801 AAAAAACTAG GAATAATAAT AAAAAAATGG AATGATGTGG AGGAAGCTCT
1851 TTACTCTT*TG* *AGAGGAAGTT* *tataaatTGA* *CCa*cacattt agtctatt̲at̲
1901 ̲catcacatgt̲ ̲attaa̲GACTT GACAACttgt ctttctcaca ccaaaCC*cct*
1951 *ctcctctgtt* *tcataaca*TC TGCTCTTTCT TTTTTTTCCT AAGCCCCTA
```

| Element Class | Location | Highlight | Promoter Configuration |
|---|---|---|---|
| U$SCN16 | 1447-1457 | Bold | 1 |
| U$SCN2 | 1558-1572 | Bold and underline | 1 and 3 |
| U$SCN7 | 1859-1883 | Bold and italic | 1 and 2 |
| U$SCN13 | 1883-1907 | Lower case | 1 and 3 |
| U$SCN6 | 1927-1945 | Lower case and bold | 1 and 2 |
| U$SCN30 | 1948-1968 | Lower case and italic | 1 and 3 |
| P$OPAQ | 1899-1915 | Lower case and underline | 2 and 3 |
| U$SCN14 | 1699-1719 | underline | 3 |

Figure 2

SEQ ID NO:2

```
   1    GGACAACATT GTTAAGAGGA GATAAGAGAT ATAGGAAGCT TCTTTTGCTG
  51    CGTTTCCTCT TCTTGAATCA ATAGTTCCAT ACAAAATGGC ATTATGATCA
 101    AACTAGGTTA AGAAGAAATG CAAAAAGGA  ACAACTAAAA ATAGGTCAAA
 151    ATTAAATAAT GAAAAGAACA AGAACAATTA ATTTTCTCT  TCTCAAATCG
 201    ATATCAAATT CTCAATAGAC TTTGGTGATG GGTTTGTCTT CTGTTCTGTT
 251    CTGTTCTGTC AATTCAAGAT TTCTTTTCCC CTCTCTCTCT TTTTCTGTTG
 301    TTGTTTGTCT CTCTTTTTTC TTATGGCTAT TGCATGTTGA CCTGGTATTG
 351    AGAGAAACAG AAAATGAACC TCAGATTTGT TAAGTCAATA TTTAGAAAGA
 401    AAAATGGATA CTTGTCGGAA CAAAAAGGG  TCCGAGTTTT TCTCGACCCG
 451    ATTCTATTTT TGGTTGATTT TTTGGGGTTC AAATTTGTTA TTATATTTTT
 501    TCTAAGTAAT TTAAGGTGTT TACGACGACG TATGTGGATT GCTCATAAAA
 551    TCTAAAATAA TGTGGGTTCA CCAAATCAAG AATCTAAAGA GACAATTTTC
 601    TAGTTATCTT TATATATATG TTTGTATTTG CCATTTAGAA GTTTAGAACT
 651    CAAAACTCAG TTCTTACAAT GCTAGCTATA ATTTGCATGA AAATAGAAAA
 701    TGATATTTTC GTGTCTTCTT TTTTTTTTGG CAGATTTTTG TGAAAAATAT
 751    CTTTAAACCA CACTTGTTAA TTATAAAACA CAGAAATATG TTTATGTTGC
 801    ACTGGCCCTC AGTTCGTGA  CGTGTTGTAA AGCTGGTATA CGTACGTATA
 851    GGTTCCGGGA AGAAACTAGT TTTAAATGAA TTACAAATG  TTTTTTAAGT
 901    AGTGAATTAG TACTAATCAC CTCGTAACCC TAAATTAATA ACATAATACA
 951    GCAATAAACA ATTCTTAAAC GAGTGGTTAA CTAGCAAATT ACGTTAACTC
1001    CTTAACCAAC CAACGGGAAA AAACAAAACC ATAATATTAA AAAACAAAGG
1051    GAACGATCGA CTGATTAGTC GAGAAGCAGA ACTTGTGGGC TTCGTGCACA
1101    CACGTAATCA CGTATAATGA ATTTATTCTA TATGTAATTA TGTATTAATA
1151    CTTTTACCTT TGTTTTATGA CTAAATTATT ATGCATGCTT GAAGTCGCTT
1201    TTAGGTCTAA TAGAAAAAGA ATCTGCCGAC TTACTAGAGA GTACTGAGTA
1251    GAGACTAGAG AAGGGGTTTA TCCATTTATG TTTCATTAGG GACACTTACT
1301    GAAGTAGACC ACACGTGCGG TGTTTGGCTC GAAGCACGAC AAGATTCAGA
1351    TGAGTCATAT CACCTATACT TCTGTCAAGT AGTGACCGAC ACGTTATGAG
1401    TCCCTTTTGA TCTCTTTAGG CTTCTTCTGT TCGGTCCATT GGCCGGCGAA
1451    GTAGCGCTTG ACACTCCATA AGACCTTCGA ATATCATTAT ATAACTAATA
1501    ACTTGCACAA TGTAGTTCAC TGTTGTAATA AATGATTTAT CAAACTATCA
1551    ATGCATTCAT AATCGTGGG TTTATTCGTT TAGAGATGGT GTCAAAATAT
1601    TATATGTGAA TAGAAACTGG AACAATAATA TAATTTTTCT GTTTTTGAGA
1651    TTTATACCGA A***TGAAGGAAA tcatatatag tatact***tttc ttaacCAAAT
1701    CTAATGTACA AATGTTTTAA ATTTGCAATA ATCCAACCGC AGAGACGCGG
1751    ATTCGACGAC TCGCATGGTT CGGCGACATT GACATtagga cacgttacaa
1801    cgTACGCGAA TGAGCGTAGG CCCATTTAAA CCCATTATTA GGCCCAGTAG
1851    GTCCCACTTT TTTACCTTTG TTCCTACA   TAAACCAAAT TCGCAGAGTA
1901    AGCTGGAAAA AACACACACC CAAGTCATCT TCATCTT*ctt cctctctctt*
1951    *catctttt*AT TTTGTAATAT CTCTACCTTA ATCTCtagtt ttctcaaatg
2001    ggtAGGCTTT GGTTTTACTT TGATCCATCT TGACACTTTA ACTATCCTTC
2051    TCTTTGTGTA ACCTATCCTC TGTTTTTGCA GTGCGTTTTG TCGTGGAAAA
2101    ACCACAGATA      (SEQ ID NO:2)
```

| Element Class | Location | Highlight | Promoter Configuration |
|---|---|---|---|
| U$SCN16 | 1566-1576 | Bold | 1 |
| U$SCN2 | 1529-1543 | Bold and underline | 1 and 3 |
| U$SCN7 | 1662-1686 | Bold and italic | 1 and 2 |
| U$SCN13 | 1671-1695 | Lower case | 1 and 3 |
| U$SCN6 | 1985-2003 | Lower case and bold | 1 and 2 |
| U$SCN30 | 1938-1958 | Lower case and italic | 1 and 3 |
| P$OPAQ | 1786-1802 | Lower case and underline | 2 and 3 |
| U$SCN14 | 1583-1603 | underline | 3 |

Figure 3

SEQ ID NO:3

```
  1  CTGGTAAAGA AAACTCGCTG ATTAATGCAT AAAGAGATTA ATTTTCTATT
 51  TTATTTTTCA CAAACATAAT TTTTCAAAAG CAAGTTGTAT TTGAAGCACC
101  TCAGAAATAT TAAATGTTAG AGATTCAATC TTTGAATTTC TAATAAGAGA
151  GGGGGTTAAC TACATATTTA GTGTTTGATA GTAATTTGAG AAAAATATAT
201  TTAGTTTTGA TAGCACTTAA AAAACCCCTA GAAGAAATAA GAAGAAAGAA
251  ACAGACACTT TTCTTAACAA ATATTTGAAT CTTAATTTAC TATTTTTTA
301  TTAAAAAAAT TACTATATCA TGGTAAAGTA ACCATAAACT AACTCTTCTA
351  TTACTCAATA GTGTTGGTCA CAGAGTAATA TATCCTTAAA ACCATTCTTT
401  ACTTTTATTC AAAAAAATAA TAATCCTAAA AGCAAGGTGC TATTAAACTT
451  AATAGAATAT GATAAAGCAA GTTAGTGGCA AAATGGTCAT GAAACAAAAT
501  TATCAGTAAA AGTTCCTCAT TATTGTGAAA ACTCCTACTC CTCAAAGAAA
551  AGAAGAAGAA AAAAAAAACC TTGGAAAAGG AGGTTTCTGA GCGATTACTA
601  TGTGGTCCCT CCTACTTtct tatttagtat agttgccgaa aaGAGGTGAT
651  AATTTCGTCG GTTTATGCCC GT*GTAACCGA AGTTTATAAA TTGACCA*CAC
701  ACACACACCC TCGCTTCTTA TACGTGACTT GAACCCACCA ACGAGTAGAA
751  AACGAGTCCA TTTTTTATTT CCTTTTTTTT TCTTTATTCA AACCCTTTTT
801  TCTCCCCtat aaatccacg ttgagcaaAG GAAGCATCCA TCCAAATACA
851  CCCATAACCA TCCCTCTCTG TTCTCTTCTC TGCCTTCTCT GTGTATAACC
901  CCGTGACCCT TCTTCTCATT T*ctcattctc* ttttctttct *cacaagagt*T
951  ATTGTTATTA TTGTTATAAC TATTGTTACT ATTACTAAAC TTGGTGTAGA
```

| Element Class | Location | Highlight | Promoter Configuration |
|---|---|---|---|
| U$SCN16 | 657-667 | Bold | 1 |
| U$SCN2 | 456-470 | Bold and underline | 1 and 3 |
| U$SCN7 | 673-697 | Bold and italic | 1 and 2 |
| U$SCN13 | 618-642 | Lower case | 1 and 3 |
| U$SCN6 | 931-949 | Lower case and bold | 1 and 2 |
| U$SCN30 | 922-942 | Lower case and italic | 1 and 3 |
| P$OPAQ | 812-828 | Lower case and underline | 2 and 3 |
| U$SCN14 | 469-489 | underline | 3 |

Figure 4

SEQ ID NO:4

```
   1    CCCGTGACCC TTCTTCTCAT TTCTCATTCT CTTTTCTTTC TCACAAGAGT
  51    TATTATTATT ATTGTTATAA CTATTGTTAC TATTACTAAA CTTGGTGTAG
 101    AATGACGAAC CGTAATGTGA ATAACACCCT TGTGGAGTTG GCAATGTCGA
 151    TTTCAAACAC AAGTGCTCTA CCTAGAGCTA CGGTGCCTGG AATAATGGCC
 201    TTGCTTGGTG GGGTTTTGGG CCTACCCCAG AAGAAGCTCT TAATGAAAAC
 251    TTTGGAAGAT GGAAGTGTTA ATAAAGGAGG GACCAAAGTT ATTAACACAT
 301    GGATTGATTC AATGAGAGCC TCTTCTCCCA CACGAGTCAA ATCCACACAA
 351    AACCAAGACC CAACAAGTCC TTGGACACTT TACCACCCTT CGGCACTGAG
 401    CATGTTTGAT CAGATTGTAT GTGAGTCCAA AGGAAAGCAG ATTGTGACTT
 451    TTCTTGACTA TGATGGAACT CTCTCCCCAA TTGTTGCAGA TCCAGATAAA
 501    GCATACATGA GTAAAAAGAT GAGGACCACA TTGAAGGACT TAGCAAGGCA
 551    TTTCCCCACT GCCATCGTGA GTGGAAGGTG CCTGGACAAG GTGTATAACT
 601    TTGTAAGATT GGCAGAACTG TACTATGCTG GGAGCCATGG AATGGACATC
 651    AAGGGACCAA CAAATAAGCG AAGTACTAAG AAGGAAAATG AACAAGTGCT
 701    CTTCCAACCC GCTAGTGAAT TCTTGCCCAT GATCAATGAG GTGTACAACA
 751    TCTTGGTGGA AAAAACAAAG TCTGTCCCTG GGCTAAGGT AGAAAATAAC
 801    AAGTTTTGCT TGTCCGTGCA CTTTCGCTGT GTTGACGAAA AGAGTTGGGT
 851    GTCATTGGCT GAACAAGTGA GCTTCGTGCT CAACGAGTAC CCAAAACTTA
 901    AGCTAACTCA AGGGAGAAAA GTGCTTGAGA TTCGACCAAC CATAAAATGG
 951    GACAAGGGCA AGGCTCTTGA ATTCTTGCTA GAGTCACTGG GATATGCTAA
1001    TTCTGATAAT GTATTTCCAA TCTATATTGG GGATGATCGA ACTGATGAAG
1051    ATGCTTTTAA GGTTTTACGG AGGAGGGGTC ATGGGGTTGG GATTCTAGTT
1101    TCTAAAATTC CAAAAGAAAC TGATGCTTCC TACACTTTGC AAGATCCAAC
1151    AGAGGTTGGG CAGTTTTTGA GGCATTTGGT GGAGTGGAAA AGAACGAGTT
1201    CCCAATACCA CAAGTTGTAG ATTCTTAGAT GAATTCAGGG AAATTGACAC
1251    CAGCCCATAA TTTGGTCAAG GGGTGGTTCC AATTATATCC CTTTTCTTGT
1301    TCGAAATAGG AAATAGTGTG TTCCATAATT TAAAGTTTTA GGGAGGAACA
1351    AAGTTGAAAT AGCTAGCTAG GTTCTCTCTC TATTTTCTTT TTCTAATGTA
1401    ATCTATTCCA TCACACGTTT GCATGCGCAT GCGGATAGTG AAAGAATTGA
1451    TGTTTTATGC CGCAATTGCG AGTGGCGCGT CAACCTTCTT GCTCTGAATT
1501    GTACTTGTCG TACGTGTGGA CAATGTGGTA TTGAAATGA AAATCACCAA
1551    CAACTTCAAC TTCAAAAGGT GATTTAGACC AAAAGAAAA AAAAAAAAA
1601    AAAA    (SEQ ID NO:4)
```

Figure 5

SEQ ID NO:5

```
   1    ACTATAGGGC ACGCGTGGTC GACGGCCCGG GCTGGTAAAG AAAACTCGCT
  51    GATTAATGCA TAAAGAGATT AATTTTCTAT TTTATTTTTC ACAAACATAA
 101    TTTTTCAAAA GCAAGTTGTA TTTGAAGCAC CTCAGAAATA TTAAATGTTA
 151    GAGATTCAAT CTTTGAATTT CTAATAAGAG AGGGGGTTAA CTACATATTT
 201    AGTGTTTGAT AGTAATTTGA GAAAAATATA TTTAGTTTTG ATAGCACTTA
 251    AAAAACCCCT AGAAGAAATA AGAAGAAAGA AACAGACACT TTTCTTAACA
 301    AATATTTGAA TCTTAATTTA CTATTTTTTT ATTAAAAAAA TTACTATATC
 351    ATGGTAAAGT AACCATAAAC TAACTCTTCT ATTACTCAAT AGTGTTGGTC
 401    ACAGAGTAAT ATATCCTTAA AACCATTCTT TACTTTTATT CAAAAAAATA
 451    ATAATCCTAA AAGCAAGGTG CTATTAAACT TAATAGAATA TGATAAAGCA
 501    AGTTAGTGGC AAAATGGTCA TGAAACAAAA TTATCAGTAA AAGTTCCTCA
 551    TTATTGTGAA AACTCCTACT CCTCAAAGAA AAGAAGAAGA AAAAAAAAAC
 601    CTTGGAAAAG GAGGTTTCTG AGCGATTACT ATGTGGTCCC TCCTACTTTC
 651    TTATTTAGTA TAGTTGCCGA AAAGAGGTGA TAATTTCGTC GGTTTATGCC
 701    CGTGTAACCG AAGTTTATAA ATTGACCACA CACACACACC CTCGCTTCTT
 751    ATACGTGACT TGAACCCACC AACGAGTAGA AAACGAGTCC ATTTTTTATT
 801    TCCTTTTTTT TTCTTTATTC AAACCCTTTT TTCTCCCCTA TAAATTCCAC
 851    GTTGAGCAAA GGAAGCATCC ATCCAAATAC ACCCATAACC ATCCCTCTCT
 901    GTTCTCTTCT CTGCCTTCTC TGTGTATAAC CCCGTGACCC TTCTTCTCAT
 951    TTCTCATTCT CTTTTCTTTC TCACAAGAGT TATTGTTATT ATTGTTATAA
1001    CTATTGTTAC TATTACTAAA CTTGGTGTAG AATGACGAAC CGTAATGTGA
1051    ATAACACCCT TGTGGAGTTG GCAATGTCGA TTTCAAACAC AAGTGCTCTA
1101    CCTAG      (SEQ ID NO:5)
```

Figure 9

Nematode infected:

| Construct | Root tip | Vascular | Cortical | Syncytia |
|---|---|---|---|---|
| RAW403 | - | - | - | ++ |
| pAW284qcz | - | - | - | ++ |
| pAW281qcz | + | + | + | ++ |

Control uninfected:

| Construct | Root tip | Vascular | Cortical |
|---|---|---|---|
| RAW403 | - | - | - |
| pAW284qcz | - | - | - |
| pAW281qcz | + | + | + |

Figure 12

Nematode infected:

| Construct | Root tip | Vascular | Cortical | Syncytia |
|---|---|---|---|---|
| pAW284qcz | - | - | - | ++ |
| RAW450 | - | - | - | - |
| RAW451 | - | - | - | + |

Control uninfected:

| Construct | Root tip | Vascular | Cortical |
|---|---|---|---|
| pAW284qcz | - | - | - |
| RAW450 | - | - | - |
| RAW451 | - | - | - |

Figure 13

PROMOTER CONFIGURATION 1:

| Element Class | U$SCN16 | U$SCN2 | U$SCN7 | U$SCN13 | U$SCN6 | U$SCN30 |
|---|---|---|---|---|---|---|
| SEQ ID NO:1 location | 1447-1457 | 1558-1572 | 1859-1883 | 1883-1907 | 1927-1945 | 1948-1968 |
| SEQ ID NO:2 location | 1566-1576 | 1529-1543 | 1662-1686 | 1671-1695 | 1985-2003 | 1938-1958 |
| SEQ ID NO:3 location | 657-667 | 456-470 | 673-697 | 618-642 | 931-949 | 922-942 |

PROMOTER CONFIGURATION 2:

| Element class | U$SCN7 | P$OPAQ | U$SCN6 |
|---|---|---|---|
| SEQ ID NO:1 location | 1859-1883 | 1899-1915 | 1927-1945 |
| SEQ ID NO:2 location | 1662-1686 | 1786-1802 | 1985-2003 |
| SEQ ID NO:3 location | 673-697 | 812-828 | 931-949 |

PROMOTER CONFIGURATION 3:

| Element class | U$SCN2 | U$SCN14 | U$SCN13 | P$OPAQ | U$SCN30 |
|---|---|---|---|---|---|
| SEQ ID NO:1 location | 1558-1572 | 1699-1719 | 1883-1907 | 1899-1915 | 1948-1968 |
| SEQ ID NO:2 location | 1529-1543 | 1583-1603 | 1671-1695 | 1786-1802 | 1938-1958 |
| SEQ ID NO:3 location | 456-470 | 469-489 | 618-642 | 812-828 | 922-942 |

Figure 14

| Common Primer | SEQ ID NO: | Sequence 5' to 3' |
|---|---|---|
| At1g35910prF | 6 | CCCGGGGTAGTGCCCTTCATGGATAC |
| At1g35910prR | 7 | GGCGCGCCTAGGGGCTTAGGAAAAAAAGAAAGAG |
| At5g10100prF | 8 | CCCGGGGGACAACATTGTTAAGAGGAG |
| At5g10100prR | 9 | GGCGCGCCTATCTGTGGTTTTTCCACGAC |
| 48986355GW | 10 | CAAGGCCATTATTCCAGGCACCGTAGCTC |
| 48986355GWnest | 11 | CTAGGTAGAGCACTTGTGTTTGAAATCGAC |
| AP1 | 12 | GTAATACGACTCACTATAGGGC |
| AP2 | 13 | ACTATAGGGCACGCGTGGT |
| 48986355prF | 14 | CCTTACTATAGGGCACG |
| 48986355prR | 15 | GGCGCGCCTCTACACCAAGTTTAGTAATAG |
| At1g35910pr986bpF | 16 | GCATCTGCAGCACATGTCAACTTGTAAAC |
| At1g35910pr502bpF | 17 | GCATCTGCAGGATACAAGGTTTTGCTC |
| At1g35910prR2 | 18 | GCTTGACGTCTAGGGGCTTAGG |

Figure 15a

```
SEQ ID NO:5 #1       ACTATAGGGC ACGCGTGGTC GACGGCCCGG GCTGGTAAAG AAAACTCGCT

SEQ ID NO:5 #51      GATTAATGCA TAAAGAGATT AATTTTCTAT TTTATTTTTC ACAAACATAA

SEQ ID NO:5 #101     TTTTTCAAAA GCAAGTTGTA TTTGAAGCAC CTCAGAAATA TTAAATGTTA

SEQ ID NO:5 #151     GAGATTCAAT CTTTGAATTT CTAATAAGAG AGGGGGTTAA CTACATATTT

SEQ ID NO:5 #201     AGTGTTTGAT AGTAATTTGA GAAAAATATA TTTAGTTTTG ATAGCACTTA

SEQ ID NO:5 #251     AAAAACCCCT AGAAGAAATA AGAAGAAAGA AACAGACACT TTTCTTAACA

SEQ ID NO:5 #301     AATATTTGAA TCTTAATTTA CTATTTTTTT ATTAAAAAAA TTACTATATC

SEQ ID NO:5 #351     ATGGTAAAGT AACCATAAAC TAACTCTTCT ATTACTCAAT AGTGTTGGTC

SEQ ID NO:5 #401     ACAGAGTAAT ATATCCTTAA AACCATTCTT TACTTTTATT CAAAAAAATA

SEQ ID NO:5 #451     ATAATCCTAA AAGCAAGGTG CTATTAAACT TAATAGAATA TGATAAAGCA

SEQ ID NO:5 #501     AGTTAGTGGC AAAATGGTCA TGAAACAAAA TTATCAGTAA AAGTTCCTCA

SEQ ID NO:5 #551     TTATTGTGAA AACTCCTACT CCTCAAAGAA AAGAAGAAGA AAAAAAAAAC

SEQ ID NO:5 #601     CTTGGAAAAG GAGGTTTCTG AGCGATTACT ATGTGGTCCC TCCTACTTTC

SEQ ID NO:5 #651     TTATTTAGTA TAGTTGCCGA AAAGAGGTGA TAATTTCGTC GGTTTATGCC

SEQ ID NO:5 #701     CGTGTAACCG AAGTTTATAA ATTGACCACA CACACACACC CTCGCTTCTT

SEQ ID NO:5 #751     ATACGTGACT TGAACCCACC AACGAGTAGA AAACGAGTCC ATTTTTTATT

SEQ ID NO:5 #801     TCCTTTTTTT TTCTTTATTC AAACCCTTTT TTCTCCCCTA TAAATTCCAC

SEQ ID NO:5 #851     GTTGAGCAAA GGAAGCATCC ATCCAAATAC ACCCATAACC ATCCCTCTCT

SEQ ID NO:4 >#1>                                         CCCGTGACCC TTCTTCTCAT
SEQ ID NO:5 #901     GTTCTCTTCT CTGCCTTCTC TGTGTATAAC CCCGTGACCC TTCTTCTCAT

SEQ ID NO:4 #21      TTCTCATTCT CTTTTCTTTC TCACAAGAGT TATTATTATT ATTGTTATAA
SEQ ID NO:5 #951     TTCTCATTCT CTTTTCTTTC TCACAAGAGT TATTGTTATT ATTGTTATAA
                                                                *

SEQ ID NO:4 #71      CTATTGTTAC TATTACTAAA CTTGGTGTAG AATGACGAAC CGTAATGTGA
SEQ ID NO:5 #1001    CTATTGTTAC TATTACTAAA CTTGGTGTAG AATGACGAAC CGTAATGTGA

SEQ ID NO:4 #121     ATAACACCCT TGTGGAGTTG GCAATGTCGA TTTCAAACAC AAGTGCTCTA
SEQ ID NO:5 #1051    ATAACACCCT TGTGGAGTTG GCAATGTCGA TTTCAAACAC AAGTGCTCTA
```

Figure 15b

```
SEQ ID NO:4 #171      CCTAGAGCTA CGGTGCCTGG AATAATGGCC TTGCTTGGTG GGGTTTTGGG
SEQ ID NO:5 #1101     CCTAG

SEQ ID NO:4 #221      CCTACCCCAG AAGAAGCTCT TAATCAAAAC TTTGGAAGAT GGAAGTGTTA

SEQ ID NO:4 #271      ATAAAGGAGG GACCAAAGTT ATTAACACAT GGATTGATTC AATGAGAGCC

SEQ ID NO:4 #321      TCTTCTCCCA CACCAGTCAA ATCCACACAA AACCAACACC CAACAAGTCC

SEQ ID NO:4 #371      TTCCACACTT TACCACCCTT CGGCACTCAG CATCTTTCAT CACATTCTAT

SEQ ID NO:4 #421      GTGAGTCCAA AGGAAAGCAG ATTGTGACTT TCTTGACTA TGATGGAACT

SEQ ID NO:4 #471      CTCTCCCCAA TTGTTGCAGA TCCAGATAAA GCATACATGA GTAAAAGAT

SEQ ID NO:4 #521      GAGGACCACA TTGAAGGACT TAGCAAGGCA TTTCCCCACT GCCATCGTGA

SEQ ID NO:4 #571      GTGGAAGGTG CCTGGACAAG GTGTATAACT TTGTAAGATT GGCAGAACTG

SEQ ID NO:4 #621      TACTATGCTG GGAGCCATGG AATGGACATC AAGGGACCAA CAAATAAGCG

SEQ ID NO:4 #671      AAGTACTAAG AAGGAAAATG AACAAGTGCT CTTCCAACCC GCTAGTGAAT

SEQ ID NO:4 #721      TCTTGCCCAT GATCAATGAG GTGTACAACA TCTTGGTGGA AAAAACAAAG

SEQ ID NO:4 #771      TCTGTCCCTG GGGCTAAGGT AGAAAATAAC AAGTTTTGCT TGTCCGTGCA

SEQ ID NO:4 #821      CTTTCGCTGT GTTGACGAAA AGAGTTGGGT GTCATTGGCT GAACAAGTGA

SEQ ID NO:4 #871      GCTTCGTGCT CAACGAGTAC CCAAAACTTA AGCTAACTCA AGGGAGAAAA

SEQ ID NO:4 #921      GTGCTTGAGA TTCGACCAAC CATAAAATGG GACAAGGGCA AGGCTCTTGA

SEQ ID NO:4 #971      ATTCTTGCTA GAGTCACTGG GATATGCTAA TTCTGATAAT GTATTTCCAA

SEQ ID NO:4 #1021     TCTATATTGG GGATGATCGA ACTGATGAAG ATGCTTTTAA GGTTTTACGG

SEQ ID NO:4 #1071     AGGAGGGGTC ATGGGGTTGG GATTCTAGTT TCTAAAATTC CAAAAGAAAC

SEQ ID NO:4 #1121     TGATGCTTCC TACACTTTGC AAGATCCAAC AGAGGTTGGG CAGTTTTTGA

SEQ ID NO:4 #1171     GGCATTTGGT GGAGTGGAAA AGAACGAGTT CCCAATACCA CAAGTTGTAG

SEQ ID NO:4 #1221     ATTCTTAGAT GAATTCAGGG AAATTGACAC CAGCCCATAA TTTGGTCAAG

SEQ ID NO:4 #1271     GGGTGGTTCC AATTATATCC CTTTTCTTGT TCGAAATAGG AAATAGTGTG
```

Figure 15c

```
SEQ ID NO:4 #1321    TTCCATAATT TAAAGTTTTA GGGAGGAACA AAGTTGAAAT AGCTAGCTAG

SEQ ID NO:4 #1371    GTTCTCTCTC TATTTTCTTT TTCTAATGTA ATCTATTCCA TCACACGTTT

SEQ ID NO:4 #1421    GCATGCGCAT GCGGATAGTG AAAGAATTGA TGTTTTATGC CGCAATTGCG

SEQ ID NO:4 #1471    AGTGGCGCGT CAACCTTCTT GCTCTGAATT GTACTTGTCG TACGTGTGGA

SEQ ID NO:4 #1521    CAATGTGGTA TTGAAAATGA AAATCACCAA CAACTTCAAC TTCAAAAGGT

SEQ ID NO:4 #1571    GATTTAGACC AAAAAGAAAA AAAAAAAAAA AAAA
```

Figure 16a

DiAlign results of TPP promoters

```
48986355pr650bp     1  ttactcaa-- ---------- ---------- ---------- ----------
At5g10100pr650bp    1  acactccata agaccttcga ATATCATTAT ATAactaata acttgcacaa
At1g35910pr650bp    1  tcattt---- ---------- ATATTATTAT ATActatcac c---------
                                              ********** ***

48986355pr650bp     9  ---------- ---------- ---------- ---------- ----------
At5g10100pr650bp   51  tgtagttcac tgttgtaata aatgatttat caaactaTCA ATGCATTCAT
At1g35910pr650bp   28  ---------- ---------- ---------- -------TCA ATTCAATGCA
                                                                *** **********

48986355pr650bp     9  ---------- ---------- TAGTGTTGGT CACAGAGTAA TATATCCTTA
At5g10100pr650bp  101  AATCTgtggg tttattcgtt TAGAGATGGT GTCAAAATAT TATATgt---
At1g35910pr650bp   41  AACCTcaaaa ta-------- ---------- ---ACACTAA TATATACACA
                       *****                 ********** ********** **********
                                                        ******* *****

48986355pr650bp    39  AAaccattc- ---------- ---------- ---------- ----------
At5g10100pr650bp  148  ---------- ---------- ---------- ---------- ----------
At1g35910pr650bp   70  AAgaaacaac agaataacac cgaagaatat aggtttagga aaatccagaa
                       **

48986355pr650bp    48  -TTTACTTTT ATTCAAAAAA Ataataatcc taaaagcaag gtgc------
At5g10100pr650bp  148  ---------- ---------- ---------- ---------- ----------
At1g35910pr650bp  220  tTTTTCTTTT AATAAAAAAA Aacacgcgac atgaaaatta tattatctca
                        ********* ********** *
                        ********* ********** *
                        ********* ********** *

48986355pr650bp    91  -------TAT TAAACTTaat agaatatgat ---------- ----------
At5g10100pr650bp  148  ---------- ---------- ---------- ---------- ----------
At1g35910pr650bp  320  gacaactTAT TAAACTTtac aagtctgcta caaatattgt caaatattta
                              *** *******

48986355pr650bp   114  ---------- -----AAAGC AAGTTAGTGG CAAAATGGTC ATGAAACAAA
At5g10100pr650bp  148  ---------- ---------- ---------- ---------- ----------
At1g35910pr650bp  370  ctaattaatg gaccaAAATC CTCTAACTTG CAAATTTGTA TCTACATCAA
                                    ***** ********** ********** **********

48986355pr650bp   149  ATTAtcagta aaagttcctc attattgtga aaactcctac tcctcaaaga
At5g10100pr650bp  148  ---------- ---------- ---------- ---------- ----------
At1g35910pr650bp  420  CTTAaaaatt aggaatatgc gacccaa--- ---------- ----------
                       ****

48986355pr650bp   199  aaagaagaag AAAAAAAAAA CCTTGGAAaa ggaggtttct gagcgattac
At5g10100pr650bp  148  ---------- ---------- ---------- ---------- ----------
At1g35910pr650bp  447  ---------- AAAAAAAAAA ACTAGGAAta ataataaaaa aatggaatg-
                                  ********** ********
                                  ********** ********
                                  ********** ********

48986355pr650bp   249  tATGTGGTCC CTCCTACTTT CTTATTTAGt atagttgccg aaaagaggtg
At5g10100pr650bp  148  ---------- ---------- ---------- ---------- ----------
At1g35910pr650bp  486  -ATGTGGAGG AAGCTCTTTA CTCTTTGAGa g--------- ----------
                        ******** ********** ********
```

Figure 16b

```
48986355pr650bp   299    ataatttcgt cggtttatgc ccgtgtaacc GAAGTTTATA AATTGACCAC
At5g10100pr650bp  148    ---------- ---------- ---------- ---------- ----------
At1g35910pr650bp  516    ---------- ---------- ---------- GAAGTTTATA AATTGACCAC
                                                          ********** **********
                                                          ********** **********
                                                          ********** **********
                                                          ********** **********
                                                          ********** **********
                                                          ********** **********
                                                          ********** **********
                                                          ********** **********
                                                          ********** **********
                                                          ********** **********

48986355pr650bp   349    ACAcacacac cctcgcttct tatacgtgac ttgaacccac caacGAGTAG
At5g10100pr650bp  148    ---------- ---------- ---------- ---------- ----GAATAG
At1g35910pr650bp  536    ACAtttagtc tattatcat- ---------- ---------- ----------
                         ***                                          ******
                         ***
                         ***
                         ***
                         ***
                         ***
                         ***
                         ***
                         ***
                         ***

48986355pr650bp   399    AAAACGAGTC CATTTTTTAT TTCCTTTTTT TTTcttt--- ----------
At5g10100pr650bp  154    AAACTGGAAC AATAATATAA TTTTTCTGTT TTTgagattt ataccgaatg
At1g35910pr650bp  555    ---------- ---------- ---------- ---------- ----------
                         ********** ********** ********** ***

48986355pr650bp   436    ---------- ---------- ---------- ---------- ----------
At5g10100pr650bp  204    aaggaaatca tatatagtat acttttctta accaaatcta atgtaCAAAT
At1g35910pr650bp  555    ---------- ---------- ---------- ---------- -----CACAT
                                                                          *****

48986355pr650bp   436    ---------- ---------- ---------- ---------- ----------
At5g10100pr650bp  254    GTTTTAAatt tgcaataatc caaccgcaga gacgcggatt cgacgactcg
At1g35910pr650bp  560    GTATTAAga- ---------- ---------- ---------- ----------
                         *******

48986355pr650bp   436    ---------- ATTCAAACCC TTTTTTCTCC CCTATAAATT CCACGTTga-
At5g10100pr650bp  354    gcgtaggccc ATTTAAACCC ATTATTAGGC CCAGTAGGTC CCACTTTttt
At1g35910pr650bp  569    ---------- ---------- ---------- ---------- ----------
                                    ********** ********** ********** *******
                                    ********** ********** ********** *******
                                    ********** ********** ********** *******

48986355pr650bp   475    ---------- ---------- ---------G CAAAGGAAGC ATCCATCCAA
At5g10100pr650bp  404    acctttgttc tcctacataa accaaattcG CAGAGTAAGC TGGAAAAAAC
At1g35910pr650bp  569    ---------- ---------- ---------- ---------- ----------
                                                         * ********** **********

48986355pr650bp   496    ATACACCCAt aaccatc--- -------CCT CTCTGTTCtc ttctctg---
At5g10100pr650bp  454    ACACACCCAa gtcatcttca tcttcttCCT CTCTCTTCat cttttatttt
At1g35910pr650bp  569    ---------- ---------- ---------- ---------- ----------
                         ********                        *** ********
```

Figure 16c

```
48986355pr650bp   533  ---------- ---------- ---------- --CCTTCTCT GTGTATAACC
At5g10100pr650bp  554  tttactttga tccatCTTGA CActttaact atCCTTCTCT TTGTGTAACC
At1g35910pr650bp  569  ---------- -----CTTGA CAa------- ---------- ----------
                                         *****  **         ******** **********
                                                           ******** **********
                                                           ******** **********

48986355pr650bp   551  ccgtgaccct TCTTCTCATT TCTCATTCTC TTTTCTTTCT CACAagagtt
At5g10100pr650bp  604  ta-------- TCCTCTGTTT TTGCAGTGCG TTTTGTcgtg gaaaaaccac
At1g35910pr650bp  577  ---------- ---------- ---------C TTGTCTTTCT CACAccaaac
                                  ********** ********** ********** ****
                                         *   ********** ********** ****
                                         *   ********** ********** ****

48986355pr650bp   601  attgttatta ttgttataac ta-------- TTGTTACTAT TACTAAACtt
At5g10100pr650bp  646  agata----- ---------- ---------- ---------- ----------
At1g35910pr650bp  598  ccctctcctc tgtttcataa catctgctct TTCTTTTTTT TCCTAAGCcc
                                                        ********** *******
```

Figure 17

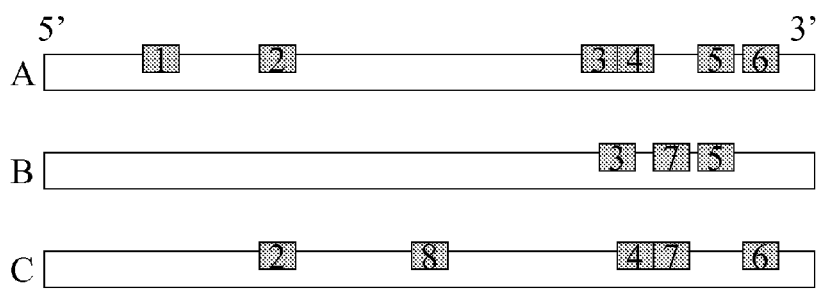

A: Representation of promoter element classes contained in bases 1349 to 1999 of
SEQ ID NO:1 comprising Promoter Configuration 1.
B: Representation of promoter element classes contained in bases 1349 to 1999 of
SEQ ID NO:1 comprising Promoter Configuration 2.
C: Representation of promoter element classes contained in bases 1349 to 1999 of
SEQ ID NO:1 comprising Promoter Configuration 3.

| Element | In Promoter | Element | Element | Element IUPAC string consensus sequence | SEQ |
|---|---|---|---|---|---|
| 1 | 1 | U$SCN16 | N/A | RTNGGTTTAKK | 19 |
| 2 | 1 and 3 | U$SCN2 | N/A | WAMATGATTAKTYWN | 20 |
| 3 | 1 and 2 | U$SCN7 | N/A | NTANNNGWWKNTTATAWATTGNYCN | 21 |
| 4 | 1 and 3 | U$SCN13 | N/A | WCWYATWTAGTMTANTWKYMKNAMN | 22 |
| 5 | 1 and 2 | U$SCN6 | N/A | TTNWYTTTCTCAMAMMWAW | 23 |
| 6 | 1 and 3 | U$SCN30 | N/A | NWTNTNCTCTNTTNTWYWTTN | 24 |
| 7 | 2 and 3 | P$OPAQ | P$O2_G | NAKWTSACRTGNMTRAN | 25 |
| 8 | 3 | U$SCN14 | N/A | NARWTRKTGKCAAAWWNKTMN | 26 |

SEQUENCE LISTING

<160> NUMBER OF SEQ ID NOS: 26

<210> SEQ ID NO 1
<211> LENGTH: 1999
<212> TYPE: DNA
<213> ORGANISM: Arabidopsis thaliana

<400> SEQUENCE: 1

```
gtagtgccct tcatggatac caaaagagaa aatttgattt agtgcataca tataacaata      60
taacgccgca taataatact gtataaaaca gtcatgtaac gatatgacag cagtaataca     120
gttccaagag acgttataat cgtatgcaat catatgcttg cgtagatttt ccaacagttt     180
tgtttcgttg ataggaggaa ctcaacactc tagggtagtg attggtagac actattagca     240
caaaaaatat taattttact ctgatgttta ccaaaaaagt taccaatcaa atatttaaga     300
gatcgtactc ttccacggcg actctaaaaa ccaaagatat aggttagact cataactact     360
ttataaagaa aatgtttaac gataactacc gagatctaat aaataaacct tcattttcaa     420
gtatattata tttgcttctt ttgtttatat atcaaaccaa gttctggttt ataaaaatat     480
tagataaaac tcgtctaaat aggtaggtgt aaaataaaat tttaaatttt tatcgataat     540
atttaaaatt tgaaaagtta ataatgatcc acacattttt tctaatattt aatttagtaa     600
tttttgtatt aaataaaatt tcaatcatat acattcgatt tttctataca ttttaactat     660
ctatttctgc ataataaact gtattttcat tttatacgct tcatcttatg gatgatattt     720
aaattttaaa tagtaattca tacacttttt aatatttaat ttagtatttt cttaaatcca     780
aattttaatc ttacaattta aatatctact ttaacataat acaaatacaa tttaatttca     840
```

-continued

```
ttgtattaaa ttcaaatata atttgattat aataaaatac aatttaattc taaaaagtcc     900
atcttagatt ttaattttcc ttttagttt tgaaaattaa aaatttaaat ttattagata     960
tatatgttac ttttcagtt ttcctattta tttaagaaaa aaatatttt taacacatgt     1020
caacttgtaa acaatagact gaacacgtca ttttatatta tgtttagttt tgaaaattaa    1080
agttaattaa atatttatat ttctttttt tagcttttct aattattttt aaaatagtaa    1140
atattttaa tacaaatcaa tatctgaaca atagatttga tacataacat aatcctataa    1200
attattaact tggaaaacga tagtttatat aataaaatta ttttcttaag ttctctaacc    1260
ataacaatta aactatattt tagcgaagaa aagaagagaa taccgagaga acgcaacttg    1320
cactaaaagc taccactttg gcaaatcact catttatatt attatatact atcacctcaa    1380
ttcaatcgaa acctcaaaat aacactaata tatacacaaa gaaacaacag aataacaccg    1440
aagaatatag gttaggaaa atccagaatt tgttgagact aaagagatca aattttcgat     1500
acaaggtttt gctcaatttg tattttcata ataaaattct ttatttcacc atagacttac    1560
atgattagtt tttctttaa taaaaaaaa cacgcgacat gaaaattata ttatctcagt     1620
gttgtcgaat ttgaatttga attttgagtt aaatactaca catttgttga caacttatta    1680
aactttacaa gtctgctaca atattgtca aatatttact aattaatgga ccaaaatcct    1740
ctaacttgca aatttgtatc tacatcaact taaaaattag gaatatgcga cccaaaaaaa    1800
aaaaaactag gaataataat aaaaaatgg aatgatgtgg aggaagctct ttactctttg     1860
agaggaagtt tataaattga ccacacattt agtctattat catcacatgt attaagactt    1920
gacaacttgt ctttctcaca ccaaacccct ctcctctgtt tcataacatc tgctctttct    1980
tttttttcct aagcccta                                                 1999
```

<210> SEQ ID NO 2
<211> LENGTH: 2110
<212> TYPE: DNA
<213> ORGANISM: Arabidopsis thaliana

<400> SEQUENCE: 2

```
ggacaacatt gttaagagga gataagagat ataggaagct tcttttgctg cgtttcctct     60
tcttgaatca atagttccat acaaaatggc attatgatca aactaggtta agaagaaatg    120
caaaaaagga acaactaaaa ataggtcaaa attaaataat gaaagaaca agaacaatta    180
attttctct tctcaaatcg atatcaaatt ctcaatagac tttggtgatg ggtttgtctt    240
ctgttctgtt ctgttctgtc aattcaagat ttcttttccc ctctctctct ttttctgttg    300
ttgtttgtct ctctttttc ttatggctat tgcatgttga cctggtattg agagaaacag    360
aaaatgaacc tcagatttgt taagtcaata tttagaaaga aaaatggata cttgtcggaa    420
caaaaagggg tccgagtttt tctcgacccg attctattt tggttgattt tttgggggttc    480
aaatttgtta ttatatttt tctaagtaat ttaaggtgtt tacgacgacg tatgtggatt    540
gctcataaaa tctaaaataa tgtgggttca ccaaatcaag aatctaaaga gacaattttc    600
tagttatctt tatatatatg tttgtatttg ccatttagaa gtttagaact caaaactcag    660
ttcttacaat gctagctata atttgcatga aatagaaaa tgatattttc gtgtcttctt    720
tttttttgg cagattttg tgaaaaatat ctttaaacca cacttgttaa ttataaaaca    780
cagaaatatg tttatgttgc actggccctc agtttcgtga cgtgttgtaa agctggtata    840
cgtacgtata ggttccggga agaaactagt tttaaatgaa ttacaaaatg tttttttaagt   900
agtgaattag tactaatcac ctcgtaaccc taaattaata acataataca gcaataaaca    960
```

```
attcttaaac gagtggttaa ctagcaaatt acgttaactc cttaaccaac caacgggaaa      1020
aaacaaaacc ataatattaa aaaacaaagg gaacgatcga ctgattagtc gagaagcaga      1080
acttgtgggc ttcgtgcaca cacgtaatca cgtataatga atttattcta tatgtaatta      1140
tgtattaata cttttacctt tgttttatga ctaaattatt atgcatgctt gaagtcgctt      1200
ttaggtctaa tagaaaaaga atctgccgac ttactagaga gtactgagta gagactagag      1260
aaggggttta tccatttatg tttcattagg gacacttact gaagtagacc acacgtgcgg      1320
tgtttggctc gaagcacgac aagattcaga tgagtcatat cacctatact tctgtcaagt      1380
agtgaccgac acgttatgag tccctttga  tctctttagg cttcttctgt tcggtccatt      1440
ggccggcgaa gtagcgcttg acactccata agaccttcga atatcattat ataactaata      1500
acttgcacaa tgtagttcac tgttgtaata aatgattat  caaactatca atgcattcat      1560
aatctgtggg tttattcgtt tagagatggt gtcaaaatat tatatgtgaa tagaaactgg      1620
aacaataata taattttctc gttttgaga  tttataccga atgaaggaaa tcatatatag      1680 tatactttc  ttaaccaaat ctaatgtaca aatgttttaa atttgcaata atccaaccgc      1740
agagacgcgg attcgacgac tcgcatggtt cggcgacatt gacattagga cacgttacaa      1800
cgtacgcgaa tgagcgtagg cccatttaaa cccattatta ggcccagtag gtcccacttt      1860 tttaccttg  ttctcctaca taaaccaaat tcgcagagta agctgaaaaa aacacacacc      1920
caagtcatct tcatcttctt cctctctctt catcttttat tttgtaatat ctctaccta      1980 atctctagtt ttctcaaatg ggtaggcttt ggttttactt tgatccatct tgacacttta      2040
actatccttc tctttgtgta acctatcctc tgtttttgca gtgcgttttg tcgtggaaaa      2100
accacagata                                                             2110

<210> SEQ ID NO 3
<211> LENGTH: 1000
<212> TYPE: DNA
<213> ORGANISM: Glycine max

<400> SEQUENCE: 3
ctggtaaaga aaactcgctg attaatgcat aaagagatta attttctatt ttatttttca       60
caaacataat ttttcaaaag caagttgtat ttgaagcacc tcagaaatat taaatgttag      120
agattcaatc tttgaatttc taataagaga gggggttaac tacatattta gtgtttgata      180
gtaatttgag aaaatatat  ttagttttga tagcacttaa aaaaccccta gaagaaataa      240
gaagaaagaa acagacactt tccttaacaa atatttgaat cttaatttac tatttttta      300 ttaaaaaat  tactatatca tggtaaagta accataaact aactcttcta ttactcaata      360
gtgttggtca cagagtaata tatccttaaa accattcttt actttattc  aaaaaaataa      420 taatcctaaa agcaaggtgc tattaaactt aatagaatat gataaagcaa gttagtggca      480
aaatggtcat gaaacaaaat tatcagtaaa agttcctcat tattgtgaaa actcctactc      540
ctcaaagaaa agaagaagaa aaaaaaaacc ttggaaaagg aggtttctga gcgattacta      600
tgtggtccct cctactttct tatttagtat agttgccgaa aagaggtgat aatttcgtcg      660
gtttatgccc gtgtaaccga agtttataaa ttgaccacac acacacaccc tcgcttctta      720
tacgtgactt gaacccacca acgagtagaa aacgagtcca ttttttattt ccttttttt       780 tcttttattca aacccttttt tctcccctat aaattccacg ttgagcaaag gaagcatcca      840
tccaaataca cccataacca tccctctctg ttctcttctc tgccttctct gtgtataacc      900
ccgtgaccct tcttctcatt tctcattctc ttttctttct cacaagagtt attgttatta      960
```

```
ttgttataac tattgttact attactaaac ttggtgtaga                1000
```

<210> SEQ ID NO 4
<211> LENGTH: 1604
<212> TYPE: DNA
<213> ORGANISM: Glycine max

<400> SEQUENCE: 4

```
cccgtgaccc ttcttctcat ttctcattct cttttctttc tcacaagagt tattattatt  60
attgttataa ctattgttac tattactaaa cttggtgtag aatgacgaac cgtaatgtga  120
ataacaccct tgtggagttg caatgtcga tttcaaacac aagtgctcta cctagagcta  180
cggtgcctgg aataatggcc ttgcttggtg gggttttggg cctacccag aagaagctct  240
taatgaaaac tttggaagat ggaagtgtta ataaggagg gaccaaagtt attaacacat  300
ggattgattc aatgagagcc tcttctccca cacgagtcaa atccacacaa aaccaagacc  360
caacaagtcc ttggacactt taccacccctt cggcactgag catgtttgat cagattgtat  420
gtgagtccaa aggaaagcag attgtgactt ttcttgacta tgatggaact ctctccccaa  480
ttgttgcaga tccagataaa gcatacatga gtaaaaagat gaggaccaca ttgaaggact  540
tagcaaggca tttccccact gccatcgtga gtggaaggtg cctggacaag gtgtataact  600
ttgtaagatt ggcagaactg tactatgctg ggagccatgg aatggacatc aagggaccaa  660
caaataagcg aagtactaag aaggaaaatg aacaagtgct cttccaaccc gctagtgaat  720
tcttgcccat gatcaatgag gtgtacaaca tcttggtgga aaaacaaag tctgtccctg  780
gggctaaggt agaaaataac aagttttgct tgtccgtgca ctttcgctgt gttgacgaaa  840
agagttgggt gtcattggct gaacaagtga gcttcgtgct caacgagtac ccaaaactta  900
agctaactca agggagaaaa gtgcttgaga ttcgaccaac cataaaatgg gacaagggca  960
aggctcttga attcttgcta gagtcactgg gatatgctaa ttctgataat gtatttccaa  1020
tctatattgg ggatgatcga actgatgaag atgcttttaa ggttttacgg aggaggggtc  1080
atggggttgg gattctagtt tctaaaattc caaagaaac tgatgcttcc tacactttgc  1140
aagatccaac agaggttggg cagttttgga ggcatttggt ggagtggaaa agaacgagtt  1200
cccaatacca caagttgtag attcttagat gaattcaggg aaattgacac cagcccataa  1260
tttggtcaag gggtggttcc aattatatcc cttttcttgt tcgaaatagg aaatagtgtg  1320
ttccataatt taaagtttta gggaggaaca aagttgaaat agctagctag gttctctctc  1380
tatttctttt ttctaatgta atctattcca tcacacgttt gcatgcgcat gcggatagtg  1440
aaagaattga tgttttatgc cgcaattgcg agtggcgcgt caaccttctt gctctgaatt  1500
gtacttgtcg tacgtgtgga caatgtggta ttgaaaatga aatcaccaa caacttcaac  1560
ttcaaaaggt gatttagacc aaaaagaaaa aaaaaaaaa aaaa              1604
```

<210> SEQ ID NO 5
<211> LENGTH: 1105
<212> TYPE: DNA
<213> ORGANISM: Glycine max

<400> SEQUENCE: 5

```
actatagggc acgcgtggtc gacggcccgg gctggtaaag aaaactcgct gattaatgca  60
taaagagatt aattttctat tttatttttc acaaacataa ttttttcaaaa gcaagttgta  120
tttgaagcac ctcagaaata ttaaatgtta gagattcaat ctttgaattt ctaataagag  180
aggggggttaa ctacatattt agtgtttgat agtaatttga gaaaaatata tttagttttg  240
```

-continued

| | |
|---|---|
| atagcactta aaaaacccct agaagaaata agaagaaaga aacagacact tttcttaaca | 300 |
| aatatttgaa tcttaattta ctatttttt attaaaaaaa ttactatatc atggtaaagt | 360 |
| aaccataaac taactcttct attactcaat agtgttggtc acagagtaat atatccttaa | 420 |
| aaccattctt tacttttatt caaaaaaata ataatcctaa aagcaaggtg ctattaaact | 480 |
| taatagaata tgataaagca agttagtggc aaaatggtca tgaaacaaaa ttatcagtaa | 540 |
| aagttcctca ttattgtgaa aactcctact cctcaaagaa aagaagaaga aaaaaaaaac | 600 |
| cttggaaaag gaggtttctg agcgattact atgtggtccc tcctactttc ttatttagta | 660 |
| tagttgccga aaagaggtga taatttcgtc ggtttatgcc cgtgtaaccg aagtttataa | 720 |
| attgaccaca cacacacacc ctcgcttctt atacgtgact tgaacccacc aacgagtaga | 780 |
| aaacgagtcc attttttatt tccttttttt ttctttattc aaacccttt ttctccccta | 840 |
| taaattccac gttgagcaaa ggaagcatcc atccaaatac acccataacc atccctctct | 900 |
| gttctcttct ctgccttctc tgtgtataac cccgtgaccc ttcttctcat ttctcattct | 960 |
| cttttctttc tcacaagagt tattgttatt attgttataa ctattgttac tattactaaa | 1020 |
| cttggtgtag aatgacgaac cgtaatgtga ataacaccct tgtggagttg gcaatgtcga | 1080 |
| tttcaaacac aagtgctcta cctag | 1105 |

```
<210> SEQ ID NO 6
<211> LENGTH: 26
<212> TYPE: DNA
<213> ORGANISM: Artificial
<220> FEATURE:
<223> OTHER INFORMATION: primer sequence

<400> SEQUENCE: 6
```

| | |
|---|---|
| cccggggtag tgcccttcat ggatac | 26 |

```
<210> SEQ ID NO 7
<211> LENGTH: 35
<212> TYPE: DNA
<213> ORGANISM: Artificial
<220> FEATURE:
<223> OTHER INFORMATION: primer sequence

<400> SEQUENCE: 7
```

| | |
|---|---|
| ggcgcgccta ggggcttagg aaaaaaaga aagag | 35 |

```
<210> SEQ ID NO 8
<211> LENGTH: 27
<212> TYPE: DNA
<213> ORGANISM: Artificial
<220> FEATURE:
<223> OTHER INFORMATION: primer sequence

<400> SEQUENCE: 8
```

| | |
|---|---|
| cccgggggac aacattgtta agaggag | 27 |

```
<210> SEQ ID NO 9
<211> LENGTH: 29
<212> TYPE: DNA
<213> ORGANISM: Artificial
<220> FEATURE:
<223> OTHER INFORMATION: primer sequence

<400> SEQUENCE: 9
```

| | |
|---|---|
| ggcgcgccta tctgtggttt ttccacgac | 29 |

```
<210> SEQ ID NO 10
<211> LENGTH: 29
<212> TYPE: DNA
<213> ORGANISM: Artificial
<220> FEATURE:
<223> OTHER INFORMATION: primer sequence

<400> SEQUENCE: 10
caaggccatt attccaggca ccgtagctc                                   29

<210> SEQ ID NO 11
<211> LENGTH: 30
<212> TYPE: DNA
<213> ORGANISM: Artificial
<220> FEATURE:
<223> OTHER INFORMATION: primer sequence

<400> SEQUENCE: 11
ctaggtagag cacttgtgtt tgaaatcgac                                  30

<210> SEQ ID NO 12
<211> LENGTH: 22
<212> TYPE: DNA
<213> ORGANISM: Artificial
<220> FEATURE:
<223> OTHER INFORMATION: primer sequence

<400> SEQUENCE: 12
gtaatacgac tcactatagg gc                                          22

<210> SEQ ID NO 13
<211> LENGTH: 19
<212> TYPE: DNA
<213> ORGANISM: Artificial
<220> FEATURE:
<223> OTHER INFORMATION: primer sequence

<400> SEQUENCE: 13
actatagggc acgcgtggt                                              19

<210> SEQ ID NO 14
<211> LENGTH: 17
<212> TYPE: DNA
<213> ORGANISM: Artificial
<220> FEATURE:
<223> OTHER INFORMATION: primer sequence

<400> SEQUENCE: 14
ccttactata gggcacg                                                17

<210> SEQ ID NO 15
<211> LENGTH: 30
<212> TYPE: DNA
<213> ORGANISM: Artificial
<220> FEATURE:
<223> OTHER INFORMATION: primer sequence

<400> SEQUENCE: 15
ggcgcgcctc tacaccaagt ttagtaatag                                  30

<210> SEQ ID NO 16
<211> LENGTH: 29
<212> TYPE: DNA
<213> ORGANISM: Artificial
<220> FEATURE:
<223> OTHER INFORMATION: primer sequence

<400> SEQUENCE: 16
```
gcatctgcag cacatgtcaa cttgtaaac            29

<210> SEQ ID NO 17
<211> LENGTH: 27
<212> TYPE: DNA
<213> ORGANISM: Artificial
<220> FEATURE:
<223> OTHER INFORMATION: primer sequence

<400> SEQUENCE: 17
gcatctgcag gatacaaggt tttgctc              27

<210> SEQ ID NO 18
<211> LENGTH: 22
<212> TYPE: DNA
<213> ORGANISM: Artificial
<220> FEATURE:
<223> OTHER INFORMATION: primer sequence

<400> SEQUENCE: 18
gcttgacgtc tagggcttagg                     22

<210> SEQ ID NO 19
<211> LENGTH: 11
<212> TYPE: DNA
<213> ORGANISM: Artificial
<220> FEATURE:
<223> OTHER INFORMATION: promoter motif consensus sequence defined using
      IUPAC ambiguous code
<220> FEATURE:
<221> NAME/KEY: misc_feature
<222> LOCATION: (3)..(3)
<223> OTHER INFORMATION: n is a, c, g, or t

<400> SEQUENCE: 19
rtnggtttak k                               11

<210> SEQ ID NO 20
<211> LENGTH: 15
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (15)..(15)
<223> OTHER INFORMATION: n is a, c, g, or t

<400> SEQUENCE: 20
wamatgatta ktywn                           15

<210> SEQ ID NO 21
<211> LENGTH: 25
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (11)..(11)

```
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 21
ntannngwwk nttatawatt gnycn                                          25

<210> SEQ ID NO 22
<211> LENGTH: 25
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 22
wcwyatwtag tmtantwkym knamn                                          25

<210> SEQ ID NO 23
<211> LENGTH: 19
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (3)..(3)
<223> OTHER INFORMATION: n is a, c, g, or t

<400> SEQUENCE: 23
ttnwytttct camammwaw                                                 19

<210> SEQ ID NO 24
<211> LENGTH: 21
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
```

```
-continued

<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 24
nwtntnctct nttntwywtt n                                              21

<210> SEQ ID NO 25
<211> LENGTH: 17
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 25
nakwtsacrt gnmtran                                                   17

<210> SEQ ID NO 26
<211> LENGTH: 21
<212> TYPE: DNA
<213> ORGANISM: Artificial
<220> FEATURE:
<223> OTHER INFORMATION: promoter motif sequence defined using IUPAC
      ambiguous code
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 26
narwtrktgk caaawwnktm n                                              21
```

PATHOGEN INDUCIBLE PLANT THEHALOSE-6-PHOPHATE PHOPHATASE GENE PROMOTERS AND REGULATORY ELEMENTS

This application is a national stage application under 35 U.S.C. §371 of PCT/EP2007/063761, filed Dec. 12, 2007, which claims benefit of U.S. provisional application number 60/874,375, filed Dec. 12, 2006. The entire contents of each of the above-identified applications are incorporated herein by reference.

FIELD OF THE INVENTION

This invention relates to promoters and regulatory elements that regulate transcription of genes similar to trehalose-6-phosphate phosphatase (TPP). The promoters of TPP-like genes of the invention are useful for controlling transcription of any nucleic acid of interest in plant roots. In particular, the promoters of the invention may be used to control transcription of nucleic acids encoding agents that confer pathogen resistance to plants.

BACKGROUND OF THE INVENTION

One of the major goals of plant biotechnology is the generation of plants with advantageous novel properties, for example, to increase agricultural productivity, to increase quality in the case of foodstuffs, or to produce specific chemicals or pharmaceuticals. The plant's natural defense mechanisms against pathogens are frequently insufficient. Fungal disease alone results in annual yield loses of many billions of US dollars. The introduction of foreign genes from plants, animals or microbial sources can increase the defense. Examples are the protection of tobacco against feeding damage by insects by expressing *Bacillus thuringiensis* endotoxins under the control of the 35S CaMV promoter or the protection of tobacco against fungal infection by expressing a bean chitinase under the control of the CaMV promoter. However, most of the approaches described only offer resistance to a single pathogen or a narrow spectrum of pathogens.

A large group of biotrophic plant pathogens of enormous agro-economical importance are nematodes. Nematodes are microscopic roundworms that feed on the roots, leaves and stems of more than 2,000 row crops, vegetables, fruits, and ornamental plants, causing an estimated $100 billion crop loss worldwide. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore pathogenic on a large number of crop species. The cyst- and lesion-forming nematode species have a more limited host range, but still cause considerable losses in susceptible crops.

Pathogenic nematodes are present throughout the United States, with the greatest concentrations occurring in the warm, humid regions of the South and West and in sandy soils. Soybean cyst nematode (*Heterodera glycines*), the most serious pest of soybean plants, was first discovered in the United States in North Carolina in 1954. Some areas are so heavily infested by soybean cyst nematode (SCN) that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematode infestation can cause significant yield losses without any obvious above-ground disease symptoms. The primary causes of yield reduction are due to root damage underground. Roots infected by SCN are dwarfed or stunted. Nematode infestation also can decrease the number of nitrogen-fixing nodules on the roots, and may make the roots more susceptible to attacks by other soil-borne plant pathogens.

The nematode life cycle has three major stages: egg, juvenile, and adult. The life cycle varies between species of nematodes. For example, the SCN life cycle can usually be completed in 24 to 30 days under optimum conditions whereas other species can take as long as a year, or longer, to complete the life cycle. When temperature and moisture levels become favorable in the spring, worm-shaped juveniles hatch from eggs in the soil. Only nematodes in the juvenile developmental stage are capable of infecting soybean roots.

The life cycle of SCN has been the subject of many studies, and as such are a useful example for understanding the nematode life cycle. After penetrating soybean roots, SCN juveniles move through the root until they contact vascular tissue, at which time they stop migrating and begin to feed. With a stylet, the nematode injects secretions that modify certain root cells and transform them into specialized feeding sites. The root cells are morphologically transformed into large multinucleate syncytia (or giant cells in the case of RKN), which are used as a source of nutrients for the nematodes. The actively feeding nematodes thus steal essential nutrients from the plant resulting in yield loss. As female nematodes feed, they swell and eventually become so large that their bodies break through the root tissue and are exposed on the surface of the root.

After a period of feeding, male SCN nematodes, which are not swollen as adults, migrate out of the root into the soil and fertilize the enlarged adult females. The males then die, while the females remain attached to the root system and continue to feed. The eggs in the swollen females begin developing, initially in a mass or egg sac outside the body, and then later within the nematode body cavity. Eventually the entire adult female body cavity is filled with eggs, and the nematode dies. It is the egg-filled body of the dead female that is referred to as the cyst. Cysts eventually dislodge and are found free in the soil. The walls of the cyst become very tough, providing excellent protection for the approximately 200 to 400 eggs contained within. SCN eggs survive within the cyst until proper hatching conditions occur. Although many of the eggs may hatch within the first year, many also will survive within the protective cysts for several years.

A nematode can move through the soil only a few inches per year on its own power. However, nematode infestation can be spread substantial distances in a variety of ways. Anything that can move infested soil is capable of spreading the infestation, including farm machinery, vehicles and tools, wind, water, animals, and farm workers. Seed sized particles of soil often contaminate harvested seed. Consequently, nematode infestation can be spread when contaminated seed from infested fields is planted in non-infested fields. There is even evidence that certain nematode species can be spread by birds. Only some of these causes can be prevented.

Traditional practices for managing nematode infestation include: maintaining proper soil nutrients and soil pH levels in nematode-infested land; controlling other plant diseases, as well as insect and weed pests; using sanitation practices such as plowing, planting, and cultivating of nematode-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops; using nematicides; and planting resistant plant varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. U.S. Pat. Nos. 5,589,622 and 5,824,876 disclose eight promoters isolated from potato roots infected with *Globodera rostochiensis*: no nematode-inducible promoters from other plant species are disclosed. These promoters are purported to be useful to direct the specific expression of toxic proteins or enzymes, or the expression of antisense RNA to a target gene or to general cellular genes.

U.S. Pat. No. 5,023,179 discloses a promoter enhancer element designated ASF-1, isolated from the CaMV promoter, which is purported to enhance plant gene expression in roots.

U.S. Pat. No. 5,750,386 discloses a deletion fragment of the RB7 root specific promoter of *Nicotiana tabacum*, which is purported to be nematode-responsive.

U.S. Pat. No. 5,837,876 discloses a root cortex specific gene promoter isolated from tobacco and designated TobRD2.

U.S. Pat. No. 5,866,777 discloses a two-gene approach to retarding formation of a nematode feeding structure. The first gene, barnase, is under control of a promoter that drives expression at least in the feeding structure. The second gene, barstar, is under control of a promoter that drives expression in all of the plant's cells except the feeding structure. Feeding site-specific promoters disclosed in U.S. Pat. No. 5,866,777 include truncated versions of the Δ0.3TobRB7 and rolC promoters.

U.S. Pat. No. 5,955,646 discloses chimeric regulatory regions based on promoters derived from the mannopine synthase and octopine synthase genes of *Agrobacterium tumefaciens*, which are purported to be nematode-inducible.

U.S. Pat. No. 6,005,092 discloses the *N. tabacum* endo-1, 4-β-glucanase (Ntce17) promoter.

U.S. Pat. Nos. 6,262,344 and 6,395,963 disclose promoters isolated from *Arabidopsis thaliana*, which are purported to be nematode-inducible.

U.S. Pat. No. 6,448,471 discloses a promoter from *A. thaliana*, which is specific for nematode feeding sites.

U.S. Pat. No. 6,703,541 discloses cloning and isolation of maize peroxidase P7X gene and its promoter, the promoter is purported to be nematode inducible.

U.S. Pat. No. 6,593,513 discloses transformation of plants with barnase under control of the promoter of the *A. thaliana* endo-1,4-β-glucanase gene (cel1) to produce plants capable of disrupting nematode attack.

U.S. Pat. No. 6,906,241 discloses use of the Ntce17 promoter in combination with a heterologous nucleic acid that encodes a nematocidal or insecticidal protein.

U.S. Pat. No. 7,078,589 discloses cloning and isolation of the soybean Pyk20 gene and promoter, which are purported to be induced by SCN infection and to show strong activity in vascular tissues.

U.S. Patent Application Publication No. 2003/0167507 discloses the promoter of soybean isoflavone synthase I, which is purported to be root specific and inducible in vegetative tissue by parasite attack.

U.S. Patent Application Publication No. 2004/0078841 discloses promoter regions of the TUB-1, RPL16A, and ARSK1 promoters of *Arabidopsis thaliana* and the PSMTA promoter from *Pisum sativum*, all of which are purported to be root-specific.

U.S. Patent Application Publication No. 2004/0029167 discloses a promoter sequence of a class II caffeic acid O-methyltransferase gene from tobacco, which is purported to be inducible in response to mechanical or chemical injury or to aggression by a pathogenic agent.

U.S. Patent Application Publication No. 2005/0262585 discloses a promoter from soybean phosphoribosylformylglycinamidine ribonucleotide synthase and deletion fragments thereof, which are purported to be responsive to nematode infection.

WO 94/10320 discloses the Δ0.3TobRB7 promoter fragment from tobacco and its use with a variety of genes for nematode feeding cell-specific expression.

WO 03/033651 discloses synthetic nematode-regulated promoter sequences designated SCP1, UCP3, and SUP.

WO 2004/029222 and its US counterpart U.S. Patent Application Publication No. 2005/0070697 disclose regulatory regions from the soybean adenosine-5'-phosphate deaminase and inositol-5-phosphatase genes, for use in improving nematode resistance in plants.

None of the above-mentioned root- or feeding-site specific promoters are currently in use in commercial seed containing an anti-pathogen transgene. Although the need for such products has long been acknowledged, no one has thus far succeeded in developing pathogen-resistant plants through recombinant DNA technology. A need continues to exist for root-specific and/or nematode feeding site preferred promoters to combine with transgenes encoding agents toxic to plant parasitic pathogens.

SUMMARY OF THE INVENTION

The invention provides promoter polynucleotides suitable for use in driving expression of a second polynucleotide in plant roots which are susceptible to attack by pathogens. The promoter polynucleotides of the invention are particularly useful for making agricultural crop plants resistant to infestation by pathogens.

The present inventors have discovered that when plant gene promoters comprise certain known regulatory elements in specific orientation to each other, the promoters share the characteristic of being inducible by pathogens. Accordingly, the invention provides promoters suitable for use in driving expression of a nucleic acid in plants that are susceptible to attack by pathogens. The pathogens are preferably nematodes. The promoters of the invention are particularly useful for making agricultural crop plants resistant to infestation by pathogens.

In one embodiment, the invention provides an isolated promoter polynucleotide capable of mediating root-preferred or pathogen-inducible expression, said promoter polynucleotide having Promoter Configuration 1, wherein the promoter polynucleotide has a plus strand and a minus strand and comprises, a U$SCN2 class element comprising a polynucleotide having the sequence as set forth in SEQ ID NO:20 on the plus strand within about 215 nucleotides of a U$SCN16 class element comprising a polynucleotide having the sequence as set forth in SEQ ID NO:19 on the plus strand, a U$SCN13 class element comprising a polynucleotide having the sequence as set forth in SEQ ID NO:22 on the plus strand within about 80 nucleotides of a U$SCN7 class element comprising a polynucleotide having the sequence as set forth in SEQ ID NO:21 on the plus strand, and a U$SCN6 class element comprising a polynucleotide having the sequence as set forth in SEQ ID NO:23 on the plus strand within about 80 nucleotides of a U$SCN30 class element having the sequence as set forth in SEQ ID NO:24 on the plus strand.

In another embodiment, the invention provides an isolated promoter polynucleotide capable of mediating root-preferred or pathogen-inducible expression, said promoter polynucleotide having Promoter Configuration 2, wherein the promoter polynucleotide has a plus strand and a minus strand, and comprises, in combination and in 5' to 3' order, a U$SCN7 class element comprising a polynucleotide having the sequence as set forth in SEQ ID NO:21 on the plus strand, a P$OPAQ class element comprising a polynucleotide having the sequence as set forth in SEQ ID NO:25 on the plus strand, and a U$SCN6 class element comprising a polynucleotide having the sequence as set forth in SEQ ID NO:23 on the plus strand, wherein the P$OPAQ class element is within about 200 nucleotides of the U$SCN7 class element, the U$SCN6 class element is within about 200 nucleotides of the P$OPAQ class element, and the U$SCN7 class element is within about 400 nucleotides of the U$SCN6 class element.

In yet another embodiment, the invention concerns an isolated promoter polynucleotide capable of mediating root-preferred or pathogen-inducible expression, said promoter polynucleotide having Promoter Configuration 3, wherein the promoter polynucleotide has a plus strand and a minus strand, and comprises, in combination and in 5' to 3' order, a U$SCN2 class element comprising a polynucleotide having the sequence as set forth in SEQ ID NO:20 on the plus strand, a U$SCN14 class element comprising a polynucleotide having the sequence as set forth in SEQ ID NO:26 on the plus strand, a U$SCN13 class element comprising a polynucleotide having the sequence as set forth in SEQ ID NO:22 on the plus strand, a P$OPAQ class element comprising a polynucleotide having the sequence as set forth in SEQ ID NO:25 on the plus strand, and a U$SCN30 class element comprising a polynucleotide having the sequence as set forth in SEQ ID NO:24 on the plus strand, wherein the U$SCN14 class element is within about 200 nucleotides of the U$SCN2 class element, the U$SCN13 class element is within about 200 nucleotides of the U$SCN14 class element, the P$OPAQ class element is within about 200 nucleotides of the U$SCN13 class element, the U$SCN30 class element is within about 200 nucleotides of the second P$OPAQ class element, and the U$SCN2 class element is within about 800 nucleotides of the U$SCN30 class element.

In another embodiment, the invention provides a promoter comprising an isolated promoter polynucleotide capable of mediating root-preferred or pathogen-inducible expression, wherein the promoter polynucleotide is selected from the group consisting of a) a polynucleotide having a sequence as set forth in SEQ ID NO:1, 2, or 3; b) a polynucleotide comprising nucleotides 1557 to 1907, or nucleotides 1498 to 1999, or nucleotides 1349 to 1999 of a polynucleotide having the sequence as set forth in SEQ ID NO:1; c) a polynucleotide comprising nucleotides 1650 to 2000 or 1460 to 2110 of a polynucleotide having the sequence as set forth in SEQ ID NO:2; d) a polynucleotide comprising nucleotides 491 to 841 or nucleotides 350 to 1000 of a polynucleotide having the sequence as set forth in SEQ ID NO:3; e) a polynucleotide having at least 70% sequence identity to any of the polynucleotides of a) though d); f) a polynucleotide hybridizing under stringent conditions to any of the polynucleotides of a) though d); g) a polynucleotide comprising a biologically active portion of any of the polynucleotides of a) through d); and h) a polynucleotide comprising a fragment of at least 50 consecutive nucleotides, or at least 100 consecutive nucleotides, or at least 200 consecutive nucleotides of a polynucleotide having a sequence as set forth in SEQ ID NO: 1, 2, or 3.

The invention also relates to expression cassettes and transgenic plants which comprise the promoter polynucleotides of the invention, and to methods of producing pathogen resistant plants or controlling parasitic pathogen infestations in crops, wherein the methods employ recombinant nucleic acid constructs comprising the promoters of the invention in operative association with a nucleic acid that encodes an agent that disrupts metabolism, growth, and/or reproduction of plant parasitic pathogens, that confers or improves plant resistance to plant parasitic pathogens, or that is toxic to plant parasitic pathogens to reduce crop destruction.

BRIEF DESCRIPTION OF THE DRAWINGS

FIG. 1: Sequence of *Arabidopsis thaliana* promoter region of locus At1g35910 (pAW284) (SEQ ID NO:1; TATA box nucleotides 1871-1877 are in lower case, bold, and italic) including a table of promoter configuration element classes present in Promoter Configuration 1, Promoter Configuration 2, and Promoter Configuration 3 which are contained within approximately nucleotides 1350-1999 of the promoter as set forth in SEQ ID NO:1.

FIG. 2: Sequence of *A. thaliana* promoter region of locus At5g0100 (pAW281) (SEQ ID NO:2) including a table of promoter configuration element classes present in Promoter Configuration 1, Promoter Configuration 2, and Promoter Configuration 3 which are contained within approximately nucleotides 1461-2110 of the promoter as set forth in SEQ ID NO:2.

FIG. 3: Sequence of promoter region of *Glycine max* cDNA clone 48986355 (RAW403) (SEQ ID NO:3; TATA box nucleotides 808-814 are in lower case, bold, and italic) including a table of promoter configuration element classes present in Promoter Configuration 1, Promoter Configuration 2, and Promoter Configuration 3 which are contained within approximately nucleotides 351-1000 of the promoter as set forth in SEQ ID NO:3.

FIG. 4: sequence of *Glycine max* cDNA clone 48986355.

FIG. 5: Sequence of pAW260 genome walking derived sequence (SEQ ID NO:5).

FIG. 9: β-glucaronidase expression patterns of binary vectors pAWZ84qcz, pAW281qcz, and RAW403 in the soybean hairy root assay set forth in Example 4. Soybean cyst nematode infected hairy roots and control uninfected hairy roots were stained 12 days after SCN inoculation. The following scoring index was used: "−" for no GUS staining, "+" for weak GUS staining, "++" for strong GUS staining.

FIG. 12: β-glucuronidase expression patterns of binary vectors pAW284qcz, RAW450, and RAW451 in the soybean hairy root assay set forth in Example 7. Soybean cyst nematode infected hairy roots and control uninfected hairy roots were stained 12 days after SCN inoculation The following scoring index was used: "−" for no GUS staining, "+" for weak GUS staining, "++" for strong GUS staining.

FIG. 13: Locations of promoter element classes of Promoter Configuration 1, Promoter Configuration 2, and Promoter Configuration 3 in the *A. thaliana* promoter of locus At1g35910 (SEQ ID NO:1), *A. thaliana* promoter of locus At5g10100 (SEQ ID NO:2), and the *G. max* cDNA clone 49986355 promoter (SEQ ID NO:3).

FIG. 14: PCR primers used to obtain the promoters of SEQ ID NO:1, SEQ ID NO:2, SEQ ID NO:3, the 986 bp deletion of A. thaliana promoter of locus At1g35910 (SEQ ID NO:1), and the 502 bp deletion of A. thaliana promoter of locus At1g35910 (SEQ ID NO: 1).

FIGS. 15a-c: Sequence alignment of G. max cDNA clone 48986355 (SEQ ID NO:4) and genome walking derived G. max sequence contained in pAW260 (SEQ ID NO:5) targeting cDNA clone 48986355. The ATG start codon of G. max cDNA clone 48986355 (SEQ ID NO:4) starts at nucleotide position 102. A putative promoter region of 1000 bp is described by SEQ ID NO:3 and is derived from nucleotide positions 32 to 1031 of pAW260 sequence (SEQ ID NO:5).

FIGS. 16a-c: Genomatix DiAlign results comparing nucleotides 1350 to 1999 of SEQ ID NO:1 (corresponding to nucleotide positions 1 to 650 of At1g35910pr650 bp), nucleotides 1461 to 2110 of SEQ ID NO:2 (corresponding to nucleotide positions 1 to 650 of At5g10100pr650 bp), and nucleotides 351 to 1000 of SEQ ID NO:3 (corresponding to nucleotide positions 1 to 650 of 48986355pr650 bp). Asterisks (*) indicate the relative degree of local similarity among the input sequences. The maximum possible similarity is represented by 10 '*' signs.

FIG. 17: Spatial representation of promoter element classes found in Promoter Configuration 1, Promoter Configuration 2, and Promoter Configuration 3 (not to exact scale) including promoter element class consensus sequences. In the column entitled "Element IUPAC string consensus sequence," the following abbreviations are employed, A=adenine, C=cytosine, G=guanine, T=thymine, R=A or G, Y=C or T, M=A or C, K=G or T, W=A or T, S=C or G, and N=A, C, G, or T.

DETAILED DESCRIPTION OF PREFERRED EMBODIMENTS

Figure 6:
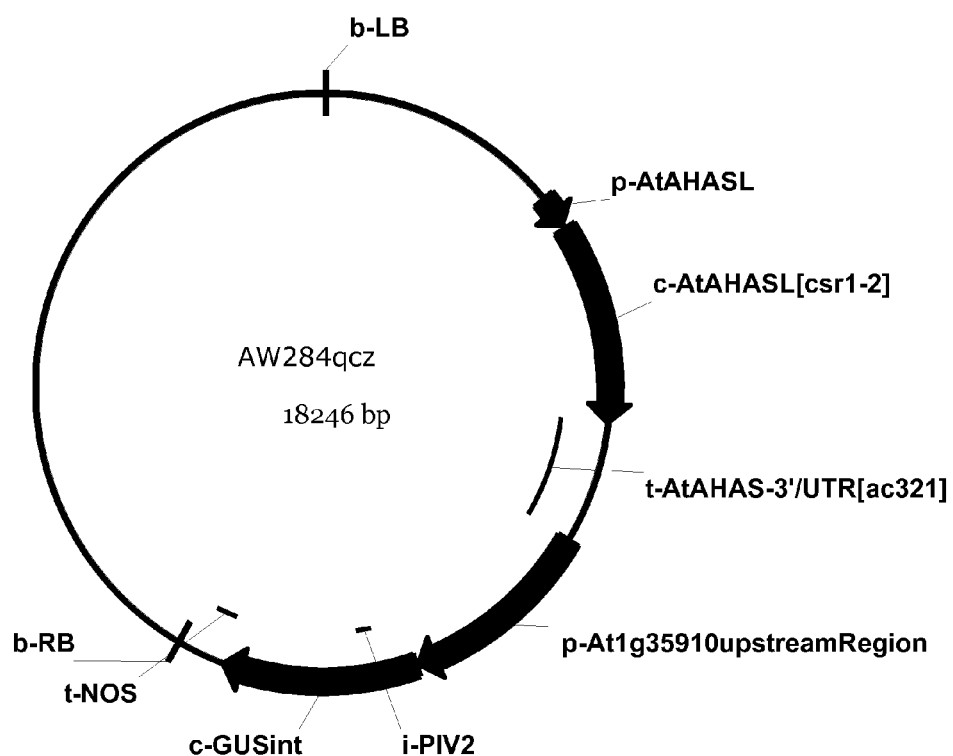
FIG. 6: Map of plasmid AW284qcz

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al, 1991 Glossary of genetics: classical and molecular, 5$^{th}$ Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook and Russell, 2001 Molecular Cloning, Third Edition, Cold Spring Harbor, Plainview, N.Y.; Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and TI, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

The promoter polynucleotides of the present invention may be provided isolated and/or purified from their natural environment, in substantially pure or homogeneous form, or free or substantially free of other nucleic acids of the species of origin. An "isolated" nucleic acid as used herein is also substantially free—at the time of its isolation—of other cellular materials or culture medium when produced by recombinant techniques, or substantially free of chemical precursors when chemically synthesized. The promoter polynucleotides of the invention are isolated polynucleotides. Where used herein, the term "isolated" encompasses all of these possibilities.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The terms "promoter" or "promoter polynucleotide" as used herein refer to a DNA sequence which, when ligated to a nucleotide sequence of interest, is capable of controlling the transcription of the nucleotide sequence of interest into mRNA. A promoter is typically, though not necessarily, located 5' (e.g., upstream) of a nucleotide of interest (e.g., proximal to the transcriptional start site of a structural gene) whose transcription into mRNA it controls, and provides a site for specific binding by RNA polymerase and other transcription factors for initiation of transcription. A "constitutive promoter" refers to a promoter that is able to express the open reading frame or the regulatory element that it controls in all or nearly all of the plant tissues during all or nearly all developmental stages of the plant. "Regulated promoter" refers to promoters that direct gene expression not constitutively, but in a temporally- and/or spatially manner, and includes both tissue-specific and inducible promoters. Different promoters may direct the expression of a gene or regulatory element in different tissues or cell types, or at different stages of development, or in response to different environmental conditions. "Tissue-specific promoter" refers to regulated promoters that are not expressed in all plant cells but only in one or more cell types in specific organs (such as roots or seeds), specific tissues (such as embryo or cotyledon), or specific cell types (such as leaf parenchyma or seed storage cells). "Inducible promoter" refers to those regulated promoters that can be turned on in one or more cell types by an external stimulus, such as a chemical, light, hormone, stress, or a pathogen.

In accordance with the invention, the promoters of the present invention may be placed in operative association with a second polynucleotide for root-specific and/or pathogen-inducible expression of the second polynucloetide in plants in order to vary the phenotype of that plant. As used herein, the terms "in operative association," "operably linked," and "associated with" are interchangeable and mean the functional linkage of a promoter polynucleotide and a second polynucleotide on a single nucleic acid fragment in such a way that the transcription of the second nucleic acid is initiated and mediated by the promoter. In general, nucleic acids that are in operative association are contiguous.

Any second polynucleotide may be placed in operative association with the promoter polynucleotides of the invention to effect root-specific or pathogen-inducible expression of the second polynucleotide. Second polynucleotides include, for example, an open reading frame, a portion of an open reading frame, a polynucleotide encoding a fusion protein, an anti-sense polynucleotide, a polynucleotide encoding a double-stranded RNA construct, a transgene, and the like. The second polynucleotide may encode an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a positive selectable marker gene, a gene affecting plant agronomic characteristics (i.e., yield), an environmental stress resistance gene (as exemplified by genes imparting resistance or tolerance to drought, heat, chilling, freezing, excessive moisture, salt stress, or oxidative stress), genes which improve starch properties or quantity, oil quantity and quality, amino acid or protein composition, and the like. The promoter polynucleotide of the invention may also be used in plants of the family Fabaceae to mediate expression in root-nodules. In this embodiment, the second polynucleotide may be a gene affecting plant agronomic characteristics such as nitrogen fixation, nitrogen transport, plant protein content, seed protein content, and the like.

Preferably, the second polynucleotide encodes a double-stranded RNA (dsRNA) or anti-sense polynucleotide, which is substantially identical or homologous in whole or in part to a plant gene required for formation or maintenance of a nematode feeding site. The second polynucleotide may alternatively encode an agent that disrupts the growth and/or reproduction of plant parasitic pathogens, that confers or improves plant resistance to plant parasitic pathogens, or that is toxic to plant parasitic pathogens to reduce crop destruction. The pathogens to be targeted are preferably plant parasitic nematodes. Any second polynucleotide encoding an agent that disrupts the growth and/or reproduction of plant parasitic pathogens, that confers or improves plant resistance to plant parasitic pathogens, or that is toxic to plant parasitic pathogens may be employed in accordance with the invention. When the pathogens are nematodes, the second polynucleotide may also encode an agent that disrupts the feeding site in plant roots e.g. by destroying or hampering the development or integrity of syncytial cells. The second polynucleotide may alternatively encode a double-stranded RNA that is substantially identical to a target gene of a parasitic plant nematode that is essential for metabolism, survival, metamorphosis, or reproduction of the nematode. The second polynucleotide may encode a double-stranded RNA that is substantially identical to a plant gene of a feeding site in plant roots, which leads to the disruption of the survival of nematodes.

As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95-99% identical or absolutely identical to 20 or more contiguous nucleotides of the target gene. Exemplary plant parasitic nematode target genes are set forth, for example, in commonly assigned co-pending U.S. Patent Application Publication No. 2005/188438, incorporated herein by reference.

Alternatively, for pathogen control, the second polynucleotide placed in operative association with the promoter polynucleotide of the invention may encode a pathogen-toxic protein, preferably a protein toxic to nematodes. For example, nucleic acids encoding microbial toxins or fragments thereof, polypeptide toxins or fragments thereof derived from insects such as those described in U.S. Pat. Nos. 5,457,178; 5,695, 954; 5,763,568; 5,959,182; and the like, are useful in this embodiment of the invention.

Crop plants and corresponding pathogenic nematodes are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). For example, plant parasitic nematodes that are targeted by the present invention include, without limitation, cyst nematodes and root-knot nematodes. Specific plant parasitic nematodes which are targeted by the present invention include, without limitation, *Heterodera glycines*, *Heterodera schachtii*, *Heterodera avenae*, *Heterodera oryzae*, *Heterodera cajani*, *Heterodera trifolii*, *Globodera pallida*, *G. rostochiensis*, or *Globodera tabacum*, *Meloidogyne incognita*, *M. arenaria*, *M. hapla*, *M. javanica*, *M. naasi*, *M. exigua*, *Ditylenchus dipsaci*, *Ditylenchus angustus*, *Radopholus similis*, *Radopholus citrophilus*, *Helicotylenchus multicinctus*, *Pratylenchus coffeae*, *Pratylenchus brachyurus*, *Pratylenchus vulnus*, *Paratylenchus curvitatus*, *Paratylenchus zeae*, *Rotylenchulus reniformis*, *Paratrichodorus anemones*, *Paratrichodorus minor*, *Paratrichodorus christiei*, *Anguina tritici*, *Bidera avenae*, *Subanguina radicicola*, *Hoplolaimus seinhorsti*, *Hoplolaimus Columbus*, *Hoplolaimus galeatus*, *Tylenchulus semipenetrans*, *Hemicycliophora arenaria*, *Rhadinaphelenchus cocophilus*, *Belonolaimus longicaudatus*, *Trichodorus prim itivus*, *Nacobbus aberrans*, *Aphelenchoides besseyi*, *Hemicriconemoides kanayaensis*, *Tylenchorhynchus claytoni*, *Xiphinema americanum*, *Cacopaurus pestis*, and the like.

In one embodiment, the targeted nematodes belong to the nematode families inducing feeding or syncytial cells. Nematode families inducing feeding or syncytial cells are Longidoridae, Trichodoridae, Heterodidae, Meloidogynidae, Pratylenchidae or Tylenchulidae. Preferably they belong to the family Heterodidae or Meloidogynidae.

Accordingly, in another embodiment the targeted nematodes belong to one or more genus selected from the group of *Cactodera*, *Dolichodera*, *Globodera*, *Heterodera*, *Punctodera*, *Longidorus*, or *Meloidogyne*. In a preferred embodiment the targeted nematodes belong to one or more genus selected from the group of *Cactodera*, *Dolichodera*, *Globodera*, *Heterodera*, *Punctodera*, or *Meloidogyne*. In a more preferred embodiment the targeted nematodes belong to one or more genus selected from the group of *Globodera, Heterodera*, or *Meloidogyne*. In an even more preferred embodiment the targeted nematodes belong to one or both genus selected from the group of *Globodera* or *Heterodera*. In another embodiment the targeted nematodes belong to the genus *Meloidogyne*.

The genus *Globodera* and *Heterodera* are preferred genus in the nematode family Heterodidae. Accordingly n one embodiment the targeted nematode belongs to one or more species selected from the group of *Globodera achilleae, Globodera artemisiae, Globodera hypolysi, Globodera mexicana, Globodera millefolii, Globodera mali, Globodera pallida, Globodera rostochiensis, Globodera tabacum* and *Globodera virginiae*. In a preferred embodiment the targeted nematodes belongs to at least one of the species *Globodera pallida, Globodera tabaccum* or *Globodera rostochiensis*. Accordingly, in one embodiment the targeted nematode belongs to one or more species selected from the group of *Hederodera avenae, Heterodera carotae, Heterodera ciceri, Heterodera cruciferae, Heterodera delvii, Heterodera elachista, Heterodera filipjevi, Heterodera gambiensis, Heterodera glycines, Heterodera goettingiana, Heterodera graduni, Heterodera humuli, Heterodera hordecalis, Heterodera latipons, Heterodera major, Heterodera medicaginis, Heterodera oryzicola, Heterodera pakistanensis, Heterodera rosii, Heterodera sacchari, Heterodera schachtii, Heterodera sorghi, Heterodera trifolii, Heterodera urticae, Heterodera vigni* and *Heterodera zeae*. In a preferred embodiment the targeted nematodes belongs to at least one of the species *Heterodera glycines, Heterodera avenae, Heterodera cajani, Heterodera gottingiana, Heterodera trifolii, Heterodera zeae* or *Heterodera schachtii*. In a more preferred embodiment the targeted nematodes belongs to the species *Heterodera glycines* or *Heterodera schachtii* or to both. In a most preferred embodiment the targeted nematodes belong to the species *Heterodera glycines*.

The genus *Meloidogyne* is a preferred genus in the nematode family Meloidogynidae. Accordingly, in one embodiment the targeted nematode belongs to one or more species selected from the group of *Meloidogyne acronea, Meloidogyne arabica, Meloidogyne arenaria, Meloidogyne artiellia, Meloidogyne brevicauda, Meloidogyne camelliae, Meloidogyne chitwoodi, Meloidogyne cofeicola, Meloidogyne esigua, Meloidogyne graminicola, Meloidogyne hapla, Meloidogyne incognita, Meloidogyne indica, Meloidogyne inornata, Meloidogyne javanica, Meloidogyne lini, Meloidogyne mali, Meloidogyne microcephala, Meloidogyne microtyla, Meloidogyne naasi, Meloidogyne salasi* and *Meloidogyne thamesi*. In a preferred embodiment the targeted nematodes belongs at least one of the species *Meloidogyne javanica, Meloidogyne incognita, Meloidogyne hapla, Meloidogyne arenaria* or *Meloidogyne chitwoodi*.

Any plant species can be transformed with the promoter polynucleotides of the invention. For example, plants which may be transformed with the nucleic acid constructs containing the promoter polynucleotides of the present invention include, without limitation, plants from a genus selected from the group consisting of *Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Zea, Triticum, Triticale, Secale, Lolium, Hordeum, Glycine, Pseudotsuga, Kalanchoe, Beta, Helianthus, Nicotiana, Cucurbita, Rosa, Fragaria, Lotus, Medicago, Onobrychis, trifolium, Trigonella, Vigna, Citrus, Linum, Geranium, Manihot, Daucus, Raphanus, Sinapis, Atropa, Datura, Hyoscyamus, Nicotiana, Petunia, Digitalis, Majorana, Ciahorium, Lactuca, Bromus, Asparagus, Antirrhinum, Heterocallis, Nemesis, Pelargonium, Panieum, Pennisetum, Ranunculus, Senecio, Salpiglossis, Browaalia, Phaseolus, Avena*, and *Allium*.

Some derivatives and variants of the promoter polynucleotides are preferably be used in particular plant clades, families, genus or plant species. Derivatives and variants of the promoter polynucleotides, which can be isolated from one plant species are preferably used in plants of the same clade, family, genus or species of plants of which the plant, used for isolation of the derivative and variant of the promoter polynucleotides, belongs to. Accordingly in one embodiment the plant is a monocotyledonous plant, preferably a plant of the family Poaceae, Musaceae, Liliaceae or Bromeliaceae, preferably of the family Poaceae. Accordingly, in yet another embodiment the plant is a Poaceae plant of the genus *Zea, Triticum, Oryza, Hordeum, Secale, Avena, Saccharum, Sorghum, Pennisetum, Setaria, Panicum, Eleusine, Miscanthus, Brachypodium, Festuca* or *Lolium*. Accordingly, in another embodiment the plant of the genus *Zea*, preferably of the species *Zea mays*. Accordingly, in one embodiment the plant is of the genus *Triticum*, preferably of the species *Triticum aestivum, Triticum speltae* or *Triticum durum*. Accordingly, in one embodiment the plant is of the genus *Oryza*, preferably of the species *Oryza sativa*. Accordingly, in one embodiment the plant is of the genus *Hordeum*, preferably of the species *Hordeum vulgare*. Accordingly, in one embodiment the plant is of the genus *Secale*, preferably of the species *Secale cereale*. Accordingly, in one embodiment the plant is of the genus *Avena*, preferably of the species *Avena sativa*. Accordingly, in one embodiment the plant is of the genus *Saccarum*, preferably of the species *Saccharum officinarum*. Accordingly, in one embodiment the plant is of the genus *Sorghum*, preferably of the species *Sorghum vulgare, Sorghum bicolor* or *Sorghum sudanense*. Accordingly, in one embodiment the plant is of the genus *Pennisetum*, preferably of the species *Pennisetum glaucum*. In one embodiment the plant is of the genus *Setaria*, preferably of the species *Setaria italica*. Accordingly, in one embodiment the plant is of the genus *Panicum*, preferably of the species *Panicum miliaceum* or *Panicum virgatum*. Accordingly, in one embodiment the plant is of the genus *Eleusine*, preferably of the species *Eleusine coracana*. Accordingly, in one embodiment the plant is of the genus *Miscanthus*, preferably of the species *Miscanthus sinensis*. Accordingly, in one embodiment the plant is of the genus *Brachypodium*, preferably of the species *Brachypodium distachyon*. Accordingly, in one embodiment the plant is a plant of the genus *Festuca*, preferably of the species *Festuca arundinaria, Festuca rubra* or *Festuca pratensis*. Accordingly, in one embodiment the plant is a plant of the genus *Lolium*, preferably of the species *Lolium perenne* or *Lolium multiflorum*. Accordingly, in one embodiment the plant is Triticosecale.

Accordingly, in one embodiment the plant is a dicotyledonous plant, preferably a plant of the family Fabaceae, Solanaceae, Brassicaceae, Chenopodiaceae, Asteraceae, Malvaceae, Linacea, Euphorbiaceae, Rosaceae, Cucurbitaceae, Theaceae, Rubiaceae, Sterculiaceae or Citrus. In one embodiment the plant is a plant of the family Fabaceae, Solanaceae or Brassicaceae. Accordingly, in one embodiment the plant is of the family Fabaceae, preferably of the genus *Glycine, Pisum, Arachis, Cicer, Vicia, Phaseolus, Lupinus, Medicago* or *Lens*. Preferred species of the family Fabaceae are *Glycine max, Pisum sativum, Arachis hypogea, Cicer arietinum, Viciafaba, Phaseolus vulgaris, Lupinus albus, Lupinus luteus, Lupinus angustifolius, Medicago sativa* or Lens culinaris. More preferred is the species *Glycine max*. Accordingly, in one embodiment the plant is of the family Solanaceae, preferably of the genus *Solanum, Lycopersicon, Nicotiana* or *Capsicum*. Preferred species of the family Solanaceae are *Solanum tuberosum, Lycopersion esculentum, Nicotiana tabaccum* or *Capsicum chinense*. More preferred is *Solanum tuberosum*. Accordingly, in one embodiment the plant is of the family Brassicaceae, preferably of the genus *Arabidopsis, Brassica* or *Raphanus*. Preferred species of the family Brassicaceae are the species *Arabidopsis thaliana, Brassica napus, Brassica oleracea, Brassica juncea* or *Brassica rapa*. More preferred is the species *Brassica napus*. Accordingly, in one embodiment the plant is of the family Chenopodiaceae, preferably of the genus *Beta*. A preferred species of the genus *Beta* is the species *Beta vulgarism*. Accordingly, in one embodiment the plant is of the family Asteraceae, preferably of the genus *Helianthus* or *Tagetes*. Preferred species of the of the genus *Helianthus* is the species *Helianthus annuus* a preferred species of the genus *Tagetes* is the species *Tagetes erecta*. Accordingly, in one embodiment the plant is of the family Malvaceae, preferably of the genus *Gossypium* or *Abelmoschus*, Preferred species of the genus *Gossypium* are the species *Gossypium hirsutum* or *Gossypium barbadense*. More preferred is the species *Gossypium hirsutum*. A preferred species of the genus *Abelmoschus* is the species *Abelmoschus esculentus*. Accordingly, in one embodiment the plant is of the family Linacea, preferably of the genus *Linum*. A preferred species of the genus *Linum* is the species *Linum usitatissimum*. Accordingly, in one embodiment the plant is of the family Euphorbiaceae, preferably of the genus *Manihot, Jatropa, Rhizinus* or *Ipomea*. Preferred species of the genus is the species *Manihot esculenta*. A preferred species of the genus *Jatropa* is *Jatropa curca*. A preferred species of the genus *Rhizinus* is *Rhizinus comunis* A preferred species of the genus *Ipomea* is *Ipomea batatas*. Accordingly, in one embodiment the plant is of the family Rosaceae, preferably of the genus *Rosa, Malus, Pyrus, Prunus, Rubus, Ribes, Vaccinium*, or *Fragaria*. A preferred species of the genus *Fragaria* is the hybrid *Fragaria x ananassa*. Accordingly, in one embodiment the plant is of the family Cucurbitaceae, preferably of the genus *Cucumis, Cirullus* or *Cucurbita*. Preferred species of the genus *Cucumis* is the species *Cucumis sativus*. A preferred species of the genus *Citrullus* is *Citrullus lanatus*. A preferred species of the genus *Cucurbita* is *Cucurbita pepo*. Accordingly, in one embodiment the plant is of the family Theaceae, preferably of the genus *Camellia*. A preferred species of the genus *Camellia* is the species *Camellia sinensis*. Accordingly, in one embodiment the plant is of the family Rubiaceae, preferably of the genus *Coffea*. A preferred species of the genus *Coffea* are the species *Coffea arabica* or *Coffea canephora*. Accordingyl, in one embodiment the plant is of the family Sterculiaceae, preferably of the genus *Theobroma*. A preferred species of the genus *Theobroma* is the species *Theobroma cacao*. Accordingly, in one embodiment the plant is of the genus *Citrus*, preferably of the Citrus species and hybrids planted in close proximity or plantations, like *Citrus sinensis, Citrus limon, Citrus reticulata, Citrus maxima*, or the like.

The *Arabidopsis* promoters of the invention (SEQ ID NO:1 and SEQ ID NO:2) represent promoter regions of *Arabidopsis* homologs of the soybean cDNA clone 48986355 (SEQ ID NO:4) encoding a polypeptide that is annotated as trehalose-6-phosphate phosphatase-like (TPP-like) protein. The *Arabidopsis* promoters were isolated from *Arabidopsis* genomic DNA as disclosed in Example 2. The soybean TPP-like promoter of this invention (SEQ ID NO:3) was isolated from soybean genomic DNA as disclosed in Example 1. As demonstrated in the Examples, when the *Arabidopsis* and soybean promoters of the invention were placed in operative association with a GUS reporter gene, the expression of GUS gene was up-regulated in soybean roots infected by nematodes.

The invention is thus embodied in a promoter comprising an isolated promoter polynucleotide having a sequence as set forth in SEQ ID NO:1, SEQ ID NO:2, or SEQ ID NO:3, or a minimal promoter polynucleotide fragment derived from an isolated promoter polynucleotide having a sequence as set forth in SEQ ID NO:1, SEQ ID NO:2, or SEQ ID NO:3 which is capable of driving root-specific or nematode-inducible expression of a second polynucleotide. The methods disclosed herein may be employed to isolate additional minimal promoter polynucleotide fragments of SEQ ID NO:1, SEQ ID NO:2, or SEQ ID NO:3 which are capable of mediating root-specific or nematode-inducible, expression of a second nucleic acid.

Alternatively, the promoter polynucleotide of the invention comprises an isolated polynucleotide which hybridizes under stringent conditions to a polynucleotide having a sequence as set forth in SEQ ID NO:1, SEQ ID NO:2, or SEQ ID NO:3, or a minimal promoter polynucleotide fragment derived from an isolated promoter polynucleotide having a sequence as set forth in SEQ ID NO:1, SEQ ID NO:2, or SEQ ID NO:3. Stringent hybridization conditions as used herein are well known, including, for example, 400 mM NaCl, 40 mM PIPES pH 6.4, 1 mM EDTA, 60° C. hybridization for 12-16 hours; followed by washing in 0.1% SDS, 0.1% SSC at approximately 65° C. for about 15-60 minutes. The invention is further embodied in an isolated promoter polynucleotide that hybridizes under stringent conditions to a polynucleotide comprising nucleotides 748 to 998, or 500 to 998, or 573 to 922 of a sequence as set forth in SEQ ID NO:1; a polynucleotide that hybridizes under stringent conditions to a promoter polynucleotide comprising nucleotides 651 to 1000 of a sequence as set forth in SEQ ID NO:2; a promoter polynucleotide that hybridizes under stringent conditions to a polynucleotide comprising nucleotides 400 to 609, or 260 to 609, or 200 to 609 of a sequence as set forth in SEQ ID NO:3; wherein the promoter polynucleotide is induced in roots of a plant infected by plant parasitic pathogens.

The promoter polynucleotide of the invention further comprises an isolated polynucleotide which has at least 50-60%, or at least 60-70%, or at least 70-80%, 80-85%, 85-90%, 90-95%, or at least 95%, 96%, 97%, 98%, 99% or more identical or similar to a promoter polynucleotide having a sequence as set forth in SEQ ID NO; 1, 2, or 3, or a minimal promoter polynucleotide fragment derived from a promoter polynucleotide having a sequence as set forth in SEQ ID NO:1, 2 or 3. The length of the sequence comparison for polynucleotides is at least 50 consecutive nucleotides, or at least 100 consecutive nucleotides, or at least 200 consecutive nucleotides up to the whole length of the sequence.

The term "sequence identity" or "identity" in the context of two polynucleotide or polypeptide sequences makes reference to those positions in the two sequences where identical pairs of symbols fall together when the sequences are aligned for maximum correspondence over a specified comparison window, for example, either the entire sequence as in a global alignment or the region of similarity in a local alignment. When percentage of sequence identity is used in reference to polypeptides it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skilled in the art. Typically this involves scoring a conservative substitution as a partial match rather than a mismatch, thereby increasing the percentage of sequence similarity.

As used herein, "percentage of sequence identity" or "sequence identity percentage" denotes a value determined by first noting in two optimally aligned sequences over a comparison window, either globally or locally, at each constituent position as to whether the identical nucleic acid base or amino acid residue occurs in both sequences, denoted a match, or does not, denoted a mismatch. As said alignment are constructed by optimizing the number of matching bases, while concurrently allowing both for mismatches at any position and for the introduction of arbitrarily-sized gaps, or null or empty regions where to do so increases the significance or quality of the alignment, the calculation determines the total number of positions for which the match condition exists, and then divides this number by the total number of positions in the window of comparison, and lastly multiplies the result by 100 to yield the percentage of sequence identity. "Percentage of sequence similarity" for protein sequences can be calculated using the same principle, wherein the conservative substitution is calculated as a partial rather than a complete mismatch. Thus, for example, where an identical amino acid is given a score of 1 and a non-conservative substitution is given a score of zero, a conservative substitution is given a score between zero and 1. The scoring of conservative substitutions can be obtained from amino acid matrices known in the art, for example, Blosum or PAM matrices.

Methods of alignment of sequences for comparison are well known in the art. The determination of percent identity or percent similarity (for proteins) between two sequences can be accomplished using a mathematical algorithm. Preferred, non-limiting examples of such mathematical algorithms are, the algorithm of Myers and Miller (Bioinformatics, 4(1):11-17, 1988), the Needleman-Wunsch global alignment (J. Mol. Biol., 48(3):443-53, 1970), the Smith-Waterman local alignment (J. Mol. Biol., 147:195-197, 1981), the search-for-similarity-method of Pearson and Lipman (PNAS, 85(8): 2444-2448, 1988), the algorithm of Karlin and Altschul (Altschul et al., J. Mol. Biol., 215(3):403-410, 1990; PNAS, 90:5873-5877, 1993). Computer implementations of these mathematical algorithms can be utilized for comparison of sequences to determine sequence identity or to identify homologs.

In addition to promoters comprising the specific isolated sequence as set forth in SEQ ID NO: 1, 2 or 3 or the minimal promoter regions contained therein, and promoter polynucleotides which hybridize under stringent conditions to promoter polynucleotides comprising a specific sequence as set forth in SEQ ID NO:1, 2, or 3, the present invention encompasses any promoter polynucleotide comprising Promoter Configuration 1, Promoter Configuration 2, or Promoter Configuration 3 as described herein. The term "Promoter Configuration" is used herein to describe a specific combination of multiple promoter element classes arranged in the 5' to 3' direction within a promoter sequence, wherein each promoter element class is in a specific spatial orientation to each other. Promoter elements can be identified in numerous ways familiar to one of skill in the art. One such method utilizes the Genomatix CoreSearch™ algorithm (Genomatix Software GmbH, Munich, Germany). The CoreSearch naming convention utilizes "P" to denote a plant based promoter element and a "U" to identify a user defined promoter element. These broad identifiers are separated from the element type by a "$". The element class follows the "$". The classes in the present invention include, "OPAQ" for a representative promoter element sequence of which several Opaque-2 like transcriptional activators bind to activate transcription and "SCN#" for a sequence conserved among multiple SCN-induced promoters, indicating an importance for SCN-induced promoter activity. The described promoter element classes are arranged in the 5' to 3' direction within a promoter DNA sequence consisting of two complementary strands of deoxyribonucleic acid. One strand is designated the "plus" strand and the complementary DNA strand is designated the "minus" strand. The DNA sequences shown by SEQ ID NO:1-3 indicate the plus strand of the double stranded DNA sequence in the 5' to 3' direction.

As indicated in FIG. 12, the U$SCN16 promoter element class designated as "Element 1" has the consensus sequence RTNGGTTTAKK (SEQ ID NO: 19), determined using Genomatix CoreSearch algorithm. The U$SCN2 promoter element class designated as "Element 2" in FIG. 12 has the consensus sequence WAMATGATTAKTYWN (SEQ ID NO:20), determined using Genomatix CoreSearch algorithm. The U$SCN7 promoter element class designated as "Element 3" in FIG. 12 has the consensus sequence NTANNNGWWKNTTATAWATTGNYCN (SEQ ID NO:21), determined using Genomatix CoreSearch algorithm. The U$SCN13 promoter element class designated as "Element 4" in FIG. 12 has the consensus sequence WCWYATWTAGTMTANTWKYMKNAMN (SEQ ID NO:22), determined using Genomatix CoreSearch algorithm. The U$SCN6 promoter element class designated as "Element 5" in FIG. 12 has the consensus sequence TTNWYTTTCTCAMAMMWAW (SEQ ID NO:23), determined using Genomatix CoreSearch algorithm. The U$SCN30 promoter element class designated as "Element 6" in FIG. 12 has the consensus sequence NWTNTNCTCTNTTNTWYWTTN (SEQ ID NO:24), determined using Genomatix CoreSearch algorithm. The P$OPAQ element class is exemplified by the element descriptor P$02_GCN4.01, which has the consensus sequence NAKWTSACRTGNMTRAN (SEQ ID NO:25), and is designated in FIG. 12 as "Element 7," see Lohmer S. et al. (1991) EMBO J. 10:617-624; Yunes J. A. et al (1998) Plant Cell 10:1941-1955; Lara P. et al (2003) J. Biol. Chem. 278:21003-21011; Muth J. R. et al (1996) Mol. Gen. Genet. 252:723-732; Onodera Y. et al (2001) J. Biol. Chem. 276:14139-14152; Schmidt R. J. et al (1992) Plant Cell 4:689-700. The U$SCN14 promoter element class designated as "Element 8" in FIG. 12 has the consensus sequence NARWTRKTGKCAAAWWNKTMN (SEQ ID NO:26), determined using Genomatix CoreSearch algorithm.

Promoter polynucleotides comprising Promoter Configuration 1 are isolated nucleic acids having a plus strand and a minus strand and comprising, a U$SCN2 class element comprising a polynucleotide having the sequence as set forth in SEQ ID NO:20 on the plus strand within about 215 nucleotides of a U$SCN16 class element comprising a polynucleotide having the sequence as set forth in SEQ ID NO:19 on the plus strand, a U$SCN13 class element comprising a polynucleotide having the sequence as set forth in SEQ ID NO:22 on the plus strand within about 80 nucleotides of a U$SCN7 class element comprising a polynucleotide having the sequence as set forth in SEQ ID NO:21 on the plus strand, and a U$SCN6 class element comprising a polynucleotide having the sequence as set forth in SEQ ID NO:23 on the plus strand within about 80 nucleotides of a U$SCN30 class element comprising a polynucleotide having the sequence as set forth in SEQ ID NO:24 on the plus strand.

In another embodiment, the invention provides a plant promoter polynucleotide comprising a nucleic acid having a plus strand and a minus strand, the nucleic acid comprising, a U$SCN2 class element comprising a polynucleotide having the sequence as set forth in SEQ ID NO:20 on the plus strand, a U$SCN16 class element comprising a polynucleotide having the sequence as set forth in SEQ ID NO:19 on the plus strand, a U$SCN13 class element comprising a polynucleotide having the sequence as set forth in SEQ ID NO:22 on the plus strand, a U$SCN7 class element comprising a polynucleotide having the sequence as set forth in SEQ ID NO:21 on the plus strand, a U$SCN6 class element comprising a polynucleotide having the sequence as set forth in SEQ ID NO:23 on the plus strand, and a U$SCN30 class element comprising a polynucleotide having the sequence as set forth in SEQ ID NO:24 on the plus strand, wherein the promoter is induced in roots of a plant infected by plant parasitic nematodes or fungi.

Promoter polynucleotides comprising Promoter Configuration 2 are isolated nucleic acids having a plus strand and a minus strand and comprising, in combination and in 5' to 3' order, a U$SCN7 class element comprising a polynucleotide having the sequence as set forth in SEQ ID NO:21 on the plus strand, a P$OPAQ class element comprising a polynucleotide having the sequence as set forth in SEQ ID NO:25 on the plus strand, and a U$SCN6 class element comprising a polynucleotide having the sequence as set forth in SEQ ID NO:23 on the plus strand, wherein the P$OPAQ class element is within about 200 nucleotides of the U$SCN7 class element, the U$SCN6 class element is within about 200 nucleotides of the P$OPAQ class element, and the U$SCN7 class element is within about 400 nucleotides of the U$SCN6 class element.

In another embodiment, the invention provides a plant promoter polynucleotide comprising a nucleic acid having a plus strand and a minus strand, the nucleic acid comprising, in combination and in 5' to 3' order, a U$SCN7 class element comprising a polynucleotide having the sequence as set forth in SEQ ID NO:21 on the plus strand, a P$OPAQ class element comprising a polynucleotide having the sequence as set forth in SEQ ID NO25 on the plus strand, and a U$SCN6 class element comprising a polynucleotide having the sequence as set forth in SEQ ID NO:23 on the plus strand, wherein the promoter is induced in roots of a plant infected by plant parasitic nematodes or fungi.

Promoter polynucleotides comprising Promoter Configuration 3 are isolated nucleic acids having a plus strand and a minus strand and comprising, in combination and in 5' to 3' order, a U$SCN2 class element comprising a polynucleotide having the sequence as set forth in SEQ ID NO:20 on the plus strand, a U$SCN14 class element comprising a polynucleotide having the sequence as set forth in SEQ ID NO:26 on the plus strand, a U$SCN13 class element comprising a polynucleotide having the sequence as set forth in SEQ ID NO:22 on the plus strand, a P$OPAQ class element comprising a polynucleotide having the sequence as set forth in SEQ ID NO:25 on the plus strand, and a U$SCN30 class element comprising a polynucleotide having the sequence as set forth in SEQ ID NO:24 on the plus strand, wherein the U$SCN14 class element is within about 200 nucleotides of the U$SCN2 class element, the U$SCN13 class element is within about 200 nucleotides of the U$SCN14 class element, the P$OPAQ class element is within about 200 nucleotides of the U$SCN13 class element, the U$SCN30 class element is within about 200 nucleotides of the second P$OPAQ class element, and the U$SCN2 class element is within about 800 nucleotides of the U$SCN30 class element.

In another embodiment, the invention provides a plant promoter polynucleotide comprising a nucleic acid having a plus strand and a minus strand, the nucleic acid comprising, in combination and in 5' to 3' order, a U$SCN2 class element comprising a polynucleotide having the sequence as set forth in SEQ ID NO:20 on the plus strand, a U$SCN14 class element comprising a polynucleotide having the sequence as set forth in SEQ ID NO:26 on the plus strand, a U$SCN13 class element comprising a polynucleotide having the sequence as set forth in SEQ ID NO:22 on the plus strand, a P$OPAQ class element comprising a polynucleotide having the sequence as set forth in SEQ ID NO:25 on the plus strand, and a U$SCN30 class element comprising a polynucleotide having the sequence as set forth in SEQ ID NO:24 on the plus strand, wherein the promoter is induced in roots of a plant by plant parasitic nematodes or fungi.

The invention further embodies "variants" or "derivatives" of the promoter of the invention. Derivatives of the specific promoter polynucleotides and their specific elements may include, but are not limited to, deletions of sequence, single or multiple point mutations, alterations at a particular restriction enzyme site, addition of functional elements, or other means of molecular modification. This modification may or may not enhance, or otherwise alter the transcription regulating activity of said sequences.

For example, one of skill in the art may delimit the functional elements or biologically active portions within the sequences and delete any non-essential elements. Functional elements or biologically active portions may be modified or combined to increase the utility or expression of the sequences of the invention for any particular application. Functionally equivalent fragments of a promoter polynucleotide of the invention can also be obtained by removing or deleting non-essential sequences without deleting the essential one. Narrowing the promoter polynucleotide sequence to its essential, transcription mediating elements can be realized in vitro by trial-and-error deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the B10BASE database "Transfac" (Biologische Datenbanken GmbH, Braunschweig; Wingender 2001) or the database PlantCARE (Lescot 2002). Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences. The term "minimal promoter" as used herein refers to a biologically active portion of a promoter polynucleotide that is capable of mediating root-specific and/or nematode-inducible expression of a second nucleic acid. Specific minimal promoter fragments of the invention include, without limitation, a promoter polynucleotide comprising nucleotides 1557 to 1907, or nucleotides 1498 to 1999, or nucleotides 1349 to 1999 of a sequence as set forth in SEQ ID NO:1, a promoter polynucleotide comprising nucleotides 1650 to 2000 or nucleotides 1460 to 2110 of a sequence as set forth in SEQ ID NO:2, and a promoter polynucleotide comprising nucleotides 491 to 841 or nucleotides 350 to 1000 of a sequence as set forth in SEQ ID NO:3, a promoter polynucleotide comprising a fragment of at least 50 consecutive nucleotides, or at least 100 consecutive nucleotides, or at least 200 consecutive nucleotides of a promoter polynucleotide having a sequence as set forth in SEQ ID NO: 1, 2, or 3.

As indicated above, deletion mutants of the promoter polynucleotide of the invention also could be randomly prepared and then assayed. With this strategy, a series of constructs are prepared, each containing a different portion of the clone (a subclone), and these constructs are then screened for activity. A suitable means for screening for activity is to attach a deleted promoter construct, which contains a deleted segment to a selectable or screenable marker, and to isolate only those cells expressing the marker gene. In this way, a number of different, deleted promoter constructs are identified which still retain the desired, or even enhanced, activity. The smallest segment, which is required for activity, is thereby identified through comparison of the selected constructs. This segment may then be used for the construction of vectors for the expression of exogenous genes.

The means for mutagenizing or creating deletions in a DNA segment encoding any promoter sequence are well known to those of skill in the art and are disclosed, for example, in U.S. Pat. No. 6,583,338, incorporated herein by reference in its entirety. One example of a regulatory sequence variant is a promoter formed by one or more deletions from a larger promoter. The 5' portion of a promoter up to the TATA box near the transcription start site can sometimes be deleted without abolishing promoter activity, as described by Zhu et al., (1995) The Plant Cell 7:1681-1689. A routine way to remove part of a DNA sequence is to use an exonuclease in combination with DNA amplification to produce unidirectional nested deletions of double-stranded DNA clones. A commercial kit for this purpose is sold under the trade name Exo-Size™. (New England Biolabs, Beverly, Mass.). Biologically active variants also include, for example, the native promoter sequences of the invention having one or more nucleotide substitutions, deletions or insertions.

Derivatives and variants also include homologs, paralogs and orthologs from other species, such as but not limited to, bacteria, fungi, and plants. "Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Paralog" refers to a polynucleotide or polypeptide that within the same species which is functionally similar. "Ortholog" refers to a polynucleotide or polypeptide that is the functional equivalent of the polynucleotide or polypeptide in another species. An orthologous gene means preferably a gene, which is encoding an orthologous protein. More specifically, the term "ortholog" denotes a polypeptide or protein obtained from one species that is the functional counterpart of a polypeptide or protein from a different species. Sequence differences among orthologs are the result of speciation.

One of the embodiments encompasses allelic variants of a promoter polynucleotide capable of mediating root-preferred and/or pathogen-inducible expression selected from the group consisting of a) a polynucleotide having a sequence as set forth in SEQ ID NO:1, 2, or 3; b) a polynucleotide comprising nucleotides 1557 to 1907, or nucleotides 1498 to 1999, or nucleotides 1349 to 1999 of a polynucleotide having the sequence as set forth in SEQ ID NO: 1; c) a polynucleotide comprising nucleotides 1650 to 2000 or nucleotides 1460 to 2110 of a polynucleotide having the sequence as set forth in SEQ ID NO:2; d) a polynucleotide comprising nucleotides 491 to 841 or nucleotides 350 to 1000 of a polynucleotide having the sequence as set forth in SEQ ID NO:3; e) a polynucleotide having at least 70% sequence identity to any of the polynucleotides of a) through d); f) a polynucleotide hybridizing under stringent conditions to any of the polynucleotides of a) through d); g) a polynucleotide comprising a biologically active portion of any of the polynucleotides of a) through d); and h) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3. As used herein, the term "allelic variant" refers to a promoter polynucleotide containing polymorphisms that lead to changes in the nucleotides of the polynucleotide and that exist within a natural population (e.g., a plant species or variety). The term "allelic variant" also refers to a polynucleotide containing polymorphisms that lead to changes in the amino acid sequences of a protein encoded by the nucleotide and that exist within a natural population. Such natural allelic variations can typically result in 1-5% variance in a polynucleotide, or 1-5% variance in the encoded protein. Allelic variants can be identified by sequencing the nucleic acid of interest in a number of different plants, which can be readily carried out by using, for example, hybridization probes to identify the same gene genetic locus in those plants. Any and all such nucleic acid variations in a polynucleotide are the result of natural allelic variation and that do not alter the functional activity of the polynucleotide are intended to be within the scope of the invention.

In another embodiment, the promoter is induced in roots of a plant exposed to a pathogen stimulus. This pathogen stimulus can be present, when the plant is infected or in the process of becoming infected by plant parasitic nematodes. A promoter mediating expression in response to a pathogen stimulus is also called a pathogen-inducible promoter. The term root-preferred expression in regard to promoters, isolated nucleic acids or polynucleotides of the invention means expression in root-tissue, in particular in root vascular tissue. In case of plants of the family Fabaceae it can also refer to expression in root-nodules. In another embodiment, the promoter is induced in root-nodules of a Fabacea plant, e.g. in root-nodules of *Glycine max*.

The invention is also embodied in expression cassettes comprising the promoter polynucleotides of the invention. "Expression cassette" in this context is to be understood broadly as comprising all sequences contained in the cassette which may influence transcription of a polynucleotide of interest and, if applicable, translation thereof. In addition to the promoter polynucleotides of the invention, the expression cassette of the invention may further comprise regulatory elements that improve the function of the promoter polynucleotide, genetic elements that allow transcription and/or translation in prokaryotic and/or eukaryotic organisms, and downstream (in 3'-direction) regulatory elements such as a transcription termination sequence and a polyadenylation sequence. The various components of the expression cassette of the invention are sequentially and operably linked together.

Accordingly, an expression cassette of the invention may comprise a promoter polynucleotide capable of mediating root-preferred or pathogen-inducible expression selected from the group consisting of a) a polynucleotide having a sequence as set forth in SEQ ID NO:1, 2, or 3; b) a polynucleotide comprising nucleotides 1557 to 1907, or nucleotides 1498 to 1999, or nucleotides 1349 to 1999 of a polynucleotide having the sequence as set forth in SEQ ID NO:1; c) a polynucleotide comprising nucleotides 1650 to 2000 or nucleotides 1460 to 2110 of a polynucleotide having the sequence as set forth in SEQ ID NO:2; d) a polynucleotide comprising nucleotides 491 to 841 or nucleotides 350 to 1000 of a polynucleotide having the sequence as set forth in SEQ ID NO:3; e) a polynucleotide having at least 70% sequence identity to any of the polynucleotides of a) through d); f) a polynucleotide hybridizing under stringent conditions to any of the polynucleotides of a) through d); g) a polynucleotide comprising a biologically active portion of any of the polynucleotides of a) through d); h) a polynucleotide comprising a fragment of at least 50 consecutive nucleotides, or at least 100 consecutive nucleotides, or at least 200 consecutive nucleotides of a polynucleotide having a sequence as set forth in SEQ ID NO:1, 2, or 3; i) a polynucleotide comprising Promoter Configuration 1 j) a polynucleotide comprising Promoter Configuration 2; and k) a polynucleotide comprising Promoter Configuration 3.

Specific genetic elements that may optionally be included in the expression cassette of the invention include, without limitation, origins of replication to allow replication in bacteria, e.g., the ORI region from pBR322 or the P15A ori; or elements required for *Agrobacterium* T-DNA transfer, such as, for example, the left and/or right borders of the T-DNA. Other components of the expression cassette of the invention may include, without limitation, additional regulatory elements such as, for example, enhancers, introns, polylinkers, multiple cloning sites, operators, repressor binding sites, transcription factor binding sites, and the like. Exemplary enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Exemplary plant intron sequences include introns from Adhl, bronzel, actinl, actin 2 (WO 00/760067), or the sucrose synthase intron; see: The Maize Handbook, Chapter 116, Freeling and Walbot, Eds., Springer, New York (1994).

Viral leader sequences may also enhance transcription of nucleic acids of interest by the expression cassette of the invention. For example, leader sequences from Tobacco Mosaic Virus (TMV), Maize Chlorotic Mottle Virus (MCMV), and Alfalfa Mosaic Virus (AMV) have been shown to be effective in enhancing expression. Other leaders known in the art include but are not limited to: Picornavirus leaders, for example, (Encephalomyocarditis virus (EMCV) leader; Potyvirus leaders, Tobacco Etch Virus (TEV) leader; MDMV leader (Maize Dwarf Mosaic Virus); Human immunoglobulin heavy-chain binding protein (BiP) leader, Untranslated leader from the coat protein mRNA of alfalfa mosaic virus (AMV RNA 4).

The expression cassette of the invention also comprises a transcription termination element or polyadenylation signal. Exemplary transcription termination elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

A second polynucleotide to be transcribed into RNA, and, optionally, expressed as a protein is inserted into the expression cassette of the invention for transformation into an organism. In accordance with the invention, the second polynucleotide is placed downstream (i.e., in 3'-direction) of the promoter of the invention and upstream of the transcription termination elements, in covalent linkage therewith. Preferably, the distance between the second polynucleotide and the promoter of the invention is not more than 200 base pairs, more preferably not more than 100 base pairs, most preferably no more than 50 base pairs.

An expression cassette of the invention may also be assembled by inserting a promoter of the invention into the plant genome. Such insertion will result in an operable linkage to a nucleic acid sequence of interest native to the genome. Such insertions allow the nucleic acid of interest to be expressed or over-expressed preferentially in root tissue, after induction by nematodes, as the result of the transcription regulating properties of the promoter of the invention. The insertion may be directed or by chance. Preferably, the insertion is directed and realized, for example, by homologous recombination. By this procedure a natural promoter may be replaced by the promoter of the invention, thereby modifying the expression profile of an endogenous gene.

The expression cassette of the invention may be inserted into a recombinant vector, plasmid, cosmid, YAC (yeast artificial chromosome), BAC (bacterial artificial chromosome), or any other vector suitable for transformation into host cell. Preferred host cells are bacterial cells, in particular *Escherichia coli*, *Agrobacterium tumefaciens* and *Agrobacterium rhizogenes* cells, and plant cells. When the host cell is a plant cell, the expression cassette or vector may become inserted into the genome of the transformed plant cell. Alternatively, the expression cassette or vector may be maintained extra chromosomally. The expression cassette or vector of the invention may be present in the nucleus, chloroplast, mitochondria, and/or plastid of the cells of the plant. Preferably, the expression cassette or vector of the invention is inserted into the chromosomal DNA of the plant cell nucleus.

The expression cassette of the invention may be transformed into a plant to provide a transgenic plant comprising one or more polynucleotides in operative association with a promoter polynucleotide of the invention. The transgenic plant of this embodiment comprises a promoter comprising a polynucleotide sequence as set forth in SEQ ID NO:1, SEQ ID NO:2, or SEQ ID NO:3, a minimal promoter fragment of SEQ ID NO:1, a minimal promoter fragment of SEQ ID NO:2, or a minimal promoter fragment of SEQ ID NO:3. Alternatively, the transgenic plant of the invention comprises a promoter polynucleotide that hybridizes under stringent conditions to a promoter comprising a nucleic acid sequence as set forth in SEQ ID NO: 1, SEQ ID NO:2, SEQ ID NO:3, a minimal promoter fragment of SEQ ID NO: 1, a minimal promoter fragment of SEQ ID NO:2, or a minimal promoter fragment of SEQ ID NO:3. Further, the transgenic plant of the invention comprises a promoter polynucleotide having at least 70% sequence identity to a polynucleotide having a sequence as set forth in SEQ ID NO: 1, SEQ ID NO:2, SEQ ID NO:3, a minimal promoter fragment of SEQ ID NO: 1, a minimal promoter fragment of SEQ ID NO:2, or a minimal promoter fragment of SEQ ID NO:3; a polynucleotide comprising a fragment of at least 50 consecutive nucleotides, or at least 100 consecutive nucleotides, or at least 200 consecutive nucleotides of a polynucleotide having a sequence as set forth in SEQ ID NO: 1, 2, or 3; a polynucleotide comprising Promoter Configuration 1; a polynucleotide comprising Promoter Configuration 2; and k) a polynucleotide comprising Promoter Configuration3.

The transgenic plants of the invention are made using transformation methods known to those of skill in the art of plant biotechnology. Any method may be used to transform the recombinant expression vector into plant cells to yield the transgenic plants of the invention. Suitable methods for transforming or transfecting host cells including plant cells can be found, for example, in WO2006/024509 (PCT/EP2005/009366; USSN60/606,0789) and in Sambrook et al. supra, and in other laboratory manuals such as Methods in Molecular Biology, 1995, Vol. 44, *Agrobacterium* protocols, Ed: Gartland and Davey, Humana Press, Totowa, N.J.

General methods for transforming dicotyledenous plants are also disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992, 375; 5,416,011; 5,569,834; 5,824,877; 6,384,301 and in EP 0301749B1. Other plant transformation methods are disclosed, for example, in U.S. Pat. Nos. 4,945,050; 5,188,958; 5,596,131; 5,981,840, and the like.

The term "plant" as used herein can, depending on context, be understood to refer to whole plants, plant cells, plant organs, plant seeds, and progeny of same. The word "plant" also refers to any plant, particularly, to seed plant, and may include, but not limited to, crop plants. Plant parts include, but are not limited to, stems, roots, shoots, fruits, ovules, stamens, leaves, embryos, meristematic regions, callus tissue, gametophytes, sporophytes, pollen, microspores, hypocotyls, cotyledons, anthers, sepals, petals, pollen, seeds and the like. The plant can be from a genus selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, prerennial grass, ryegrass, and *Arabidopsis thaliana*. In another embodiment the plant can be from a genus selected from the group consisting of citrus trees, pineapple, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula* and *Arabidopsis thaliana*. In another embodiment the plant can be from a genus selected from the group consisting of, tobacco, sunflower, pea, alfalfa, soybean, tomato, potato, cotton, tobacco, eggplant, pepper, oilseed rape, canola, beet, cabbage, cauliflower, broccoli, lettuce, *Lotus* sp., *Medicago truncatula* and *Arabidopsis thaliana*. In another embodiment the plant can be from a genus selected from the group consisting of maize, wheat, barley, sorghum, rye, triticale, rice, sugarcane, pineapple, coconut, banana, perennial grass and ryegrass.

The transgenic plants of the invention may be crossed with similar transgenic plants or with transgenic plants lacking the promoter of the invention and second nucleic acid or with non-transgenic plants, using known methods of plant breeding, to prepare seed. Further, the transgenic plant of the present invention may comprise, and/or be crossed to another transgenic plant that comprises, one or more different genes of interest operably linked to a promoter polynucleotide of the present invention or to another promoter, thus creating a "stack" of transgenes in the plant and/or its progeny. The seed is then planted to obtain a crossed fertile transgenic plant comprising the nucleic acid of interest and the promoter of the invention. The plant may be a monocot or a dicot. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the DNA construct.

"Gene stacking" can also be accomplished by transferring two or more genes into the cell nucleus by plant transformation. Multiple genes may be introduced into the cell nucleus during transformation either sequentially or in unison. Multiple genes in plants or target pathogen species can be down-regulated by gene silencing mechanisms, specifically RNAi, by using a single transgene targeting multiple linked partial sequences of interest. Stacked, multiple genes under the control of individual promoters can also be over-expressed to attain a desired single or multiple phenotype. Constructs containing gene stacks of both over-expressed genes and silenced targets can also be introduced into plants yielding single or multiple agronomically important phenotypes. In certain embodiments the nucleic acid sequences of the present invention can be stacked with any combination of polynucleotide sequences of interest to create desired phenotypes. The combinations can produce plants with a variety of trait combinations including but not limited to disease resistance, herbicide tolerance, yield enhancement, cold and drought tolerance. These stacked combinations can be created by any method including but not limited to cross breeding plants by conventional methods or by genetic transformation. If the traits are stacked by genetic transformation, the polynucleotide sequences of interest can be combined sequentially or simultaneously in any order. For example if two genes are to be introduced, the two sequences can be contained in separate transformation cassettes or on the same transformation cassette. The expression of the sequences can be driven by the same or different promoters.

The invention further comprises a crop comprising a plurality of the transgenic plants of the invention, planted together in an agricultural field.

The transgenic plants of the invention may be used in a method of controlling a plant parasitic pathogen infestation in a crop, which comprises the step of growing said crop from seeds comprising an expression cassette comprising a promoter polynucleotide of the invention in operative association with a second polynucleotide that encodes an agent that disrupts the metabolism, growth and/or reproduction of said plant parasitic pathogen, that improves plant tolerance to said plant parasitic pathogen, or that is toxic to said plant parasitic pathogen, wherein the expression cassette is stably integrated into the genomes of plant cells, plants and/or seeds. Such agents include, without limitation, a double-stranded RNA which is substantially identical to a target gene of a parasitic plant pathogen which is essential for survival, metamorphosis, or reproduction of the pathogen; a double-stranded RNA which is substantially identical to a plant gene required to maintain a nematode feeding site; an anti-sense RNA, an siRNA, an miRNA or its precursor, a protein that interferes with the metabolism, survival, metamorphosis or reproduction of the pathogen or a microbial toxin, a toxin derived from an insect, that interferes with the metabolism, survival, metamorphosis or reproduction of the pathogen, and the like.

The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Cloning TPP-Like Gene Promoters from Soybean

Soybean *Glycine max* cv. Williams 82 seeds were germinated on 1% agar plates for 3 days at 25° C. and transferred onto germination pouches with one seedling per pouch. One day later, each seedling was inoculated with 1000 second-stage juveniles (J2) of *Heterodera glycines* race3. The seedlings were maintained at the same culturing condition. The position of the root tip was marked on the pouch. One day after inoculation, the seedling was taken out and rinsed in water to remove remaining nematodes on the surface, and then transferred onto a new pouch, and the position of the root tip was marked on the pouch.

Six days after inoculation, the root portion between the two marks was sliced into 1 cm long pieces with a razor blade and immediately fixed in a solution containing 3 parts of ethanol and 1 part of glacial acidic acid. The solution was vacuumed at 400 mm Hg for 15 minutes twice and then kept on ice for 4-8 hours. The root pieces were then infiltrated by 10% sucrose for 4 hours on ice and then 15% sucrose for 4 hours on ice. During each infiltration step, the solution was first vacuumed for 15 minutes at 400 mm Hg. All sucrose solutions were DEPC (Sigma-Aldrich Corp., St. Louis, Mo.) treated to suppress RNAase activity.

The root pieces were then picked up and blotted on paper towel to remove the liquid on the surface, and then embedded in OCT (Optimum Cutting Temperature) (Sakura Finetechnical Co., Ltd., Tokyo, Japan) in a cryomold, followed by immediately freezing in liquid nitrogen. Once the OCT formed a block in the mold, it can be stored at −80° C.

The root pieces were sectioned at 10 μm longitudinally with Leica Cryostat C3050s (Leica Microsystems Nussloch GmbH, Nussloch, Germany). The temperature for the cutting is set to −15° C. Sections were transferred onto PEN (P.A.L.M. Microlaser Technologies GmbH, Bernried, Germany) slide on the membrane side and stored at −80° C.

The slides were first fixed in cold (4° C.) 70% Ethanol for 1 minute, then the OCT were dissolved by immersing the slides in 1×PBS (Mediatech Inc., Herndon, Va.) for 2 minutes, followed by dehydration in 70%, 95%, and 100% ethanol for 1 minute in each solution. The slides were then air dried and mounted onto the PALM (P.A.L.M. Microlaser Technologies GmbH, Bernried, Germany) microscope for observation. The syncytia cells were identified by their unique morphology of enlarged cell size, thickened cell wall, and dense cytoplasm. The cap of a 200 μl micro-tube was filled with 20 μl RNA extraction buffer from the kit and mounted over the sample with a holder, with the open end facing the sample. Using the computer interface of the PALM system, the cutting region was defined. Then a laser beam was fired through the slide and cut the syncytium into small pieces. At the same time, the force of the laser bean blew the cut pieces into the RNA extraction buffer above the sample. Once finished, the cap was removed from the holder and recapped onto its tube, and the RNA extraction buffer containing the cut pieces of the syncytia was spun down to the bottom of the tube.

Total cellular RNA was extracted and isolated from laser-captured cells using the PicoPure™ RNA Isolation Kit from Arcturus (Arcturus Inc., Mountain View, Calif.) following the manufacturer's instruction.

To amplify RNA from low input total RNA, RiboAmp™ HS RNA Amplification Kit from Arcturus (Arcturus Inc., Mountain View, Calif.) was used following the manufacturer's instruction, including addition of nucleic acid carrier to the input sample RNA prior to the start of RiboAmp™ HS protocol as recommended in the user guide. Successful amplification was achieved when as little as 500 pg reference RNA together with carrier nucleic acid supplied in the RiboAmp™ HS RNA Amplification Kit, were used as input in the amplification reaction.

The Soybean (*Glycine max*) cDNA PCR products representing set of genes to be interrogated are spotted robotically onto chemically modified glass support (UltraGAPS, Corning Inc., Acton, Mass.) after purification and re-suspension in 50% DMSO using a Gen III Spotter (Amersham Biosciences, Piscataway, N.J.). A control PCR plate consisted of a set of control genes (18 genes in 12 replicates) was included at the beginning of all spotting sessions, as such, the first 18 spots in the first row of each panel were external spike genes and they can be used as QC controls and/or to obtain a standard curve with which the normalized abundance for the other clones in the panel was calculated. The control genes are a commercially available set of artificial genes designed based upon sequences of the yeast inter-genic regions (Amersham Biosciences, Piscataway, N.J.).

The implementation of a set of control genes in the microarray process allowed adoption of a single color-based hybridization approach instead of the previously practiced two-color hybridization format, i.e. labeling and hybridizing a single cDNA sample to a cDNA array instead of a treatment vs reference sample pair. Consequently, normalized signal intensity, and hence absolute transcript abundance for each expressed transcript in the original RNA sample instead of ratios, can be calculated and compared between samples and across different experiments.

The amplified RNA (aRNA) samples were indirectly labeled with Cy 3 using the 3DNA Dendrimer technology of Genisphere™ as described in the random primer-based labeling protocol (Genisphere, Hatfield, Pa.) and hybridized to the soybean cDNA arrays using a two-step hybridization protocol as described in the Mfr's instruction (Genisphere, Hatfield, Pa.). cDNA products from the reverse transcription of aRNA were column-purified and its quality checked on Agilent BioAnalyzer. Purified cDNA was then ligated to capture sequences and further purified and concentrated using standard molecular biological protocols. To increase the reproducibility and cross-sample comparability, identical amount (~250 ng) of purified cDNA-capture sequence ligation mix was used to hybridize the arrays for all samples. Known amount of corresponding cDNA pre-mix for the control genes was spiked into the sample cDNA prior to hybridization and labeling. To minimize variations associated with manual hybridization, all hybridizations were performed on a Lucidea Pro Automated Slide Processor (Amersham Biosciences, Piscataway, N.J.).

Processed slides were scanned using a Gen III Scanner (Amersham Biosciences, Piscataway, N.J.). The .gel files generated from the Gen III Scanner were imported into and analyzed using feature extraction software ImaGene™ version 5.1 from BioDiscovery (Los Angeles, Calif.) in which images were segmented into pixels and converted to numeric intensity values. Local background and other QC values associated with each spot on the image were also obtained.

Raw data obtained from ImaGene™ was directly imported into a SAS-based microarray expression data analysis pipeline developed in-house and processed in the following sequential steps. Data from negative, empty and bad spots were removed from the dataset. The definition of the negative, empty and bad spots followed software developers' recommendation (BioDiscovery, Los Angeles, Calif.) as well as based on empirically determined settings for data removal. Negative spots were defined as any spots with which a negative signal value was obtained after correcting for local background. Empty spots were defined as any spots that had signal values after correcting for local background of less than $n \times SD_{background}$ where n is commonly defined as 2 or 3. Whereas bad spots were defined as any spots with CV$_{Signal\ Intensity}$ greater than an empirically defined value, which is a measure of the spot/signal morphology, foreign contamination and uniformity of the hybridization signal. All the settings have to be set before processing the images in ImaGene™ software and spots will be tagged a non-zero "flag" value indicative of the type of QC misses in the ImaGene™ output file. Only spots with a "flag" value of "0" were kept for further analyses. Retained signal measurements were normalized so that the global ground means for each array were scaled to 500.

As a prerequisite to the successful development of an approach for controlling nematode infestations, genes expressed as a result of nematode infestation of soybean roots, need to be identified. These genes include, but are not limited to, genes that are essential for the formation of syncytium and genes differentially expressed in response to SCN infection.

To identify genes specifically and/or differentially expressed in syncytia, three types of cells and root tissues were collected and used for the extraction of total cellular RNA, the syncytia, root segments not in direct contact with soybean cyst nematode but are from SCN infected soybean root designated as "non-syncytia" and untreated control roots. Total RNA was extracted, isolated from LCM captured syncytia and amplified as described above. To isolate total RNA from root segments, TRIZOL®RNA isolation kit from Invitrogen Life Technologies (Invitrogen Corporation, Carlsbad, Calif.) was used following manufacturer's recommended protocol. Total RNA was further purified using Qiagen RNeasy Midi kit (Qiagen Inc., Valencia, Calif.) as described in the manufacturer's user guide. To better compare expression data generated from LCM captured syncytia and root tissue segments, total RNA prepared from both "non-syncytia" and untreated control roots were subjected to the same 2-round RNA amplification process as described above, so it was the amplified aRNA from all three cell/tissue types of soybean roots that were compared in the final analysis.

Table 1 describes the number of LCM captured syncytia samples and "non-syncytia" and control root tissues samples collected and analyzed in this study. The information on RNA amplification and microarray hybridization was also included in this table.

TABLE 1

Tissue sample and experimental information

| Sample Name/ Treatment | Number of Samples | Number of Amplified RNA | Number of Hybridization |
|---|---|---|---|
| 6-Day Syncytia | 2 | 2 | 9 |
| 6-Day Non-Syncytia | 2 | 2 | 11 |
| 6-Day Untreated Roots | 3 | 4 | 17 |

Statistical analyses of gene expression data generated from samples of LCM captured syncytia, "non-syncytia" and control root tissues led to the identification of genes expressed specifically or differentially in syncytia. One such gene (48986355) is annotated as encoding a trehalose-6-phosphate phosphatase-like protein. Table 2 summarized the expression data as measured by cDNA microarray analysis across all three cell/tissue samples: syncytia, SCN infected non-syncytia and untreated control root tissues. Relative levels of gene expression are expressed as normalized signal intensities (±standard deviation) as described above.

TABLE 2

Expression of trehalose-6-phosphate phosphatase gene

| Gene Name | Syncytia #1(N) | Syncytia #2(N) | Non-Syncytia | Control Roots |
|---|---|---|---|---|
| 48986355 | 712 ± 90(4) | 453 ± 205(5) | ND* | ND |

N in (N) is the number of cDNA microarray measurements.
ND: Not detectable under experimental conditions described in the study.

As demonstrated in Table 2, Soybean cDNA clone 48986355 was identified as being up-regulated in syncytia of SCN-infected soybean roots. FIG. 4 depicts the sequence of soybean cDNA clone 48986355. The 48986355 cDNA sequence (SEQ ID NO:4) was determined to be full-length since there is a TAG stop codon starting at bp 87 upstream and in the same frame as the ATG start codon of the encoded trehalose-6-phosphate phosphatase open reading frame which starts at base pair 102.

To clone the promoter sequence of 48986355, the Universal Genome Walking Kit (Clontech Laboratories Inc., Palo Alto, Calif.) was used according to the manufacturer's instructions. For this, soybean (*Glycine max*, Resnik) genomic DNA was extracted using the Qiagen DNAeasy Plant Minikit (Qiagen). The procedure consisted of two PCR amplifications, using an adapter primer and a gene-specific primer for each amplification reaction. The sequences of primers used to isolate the promoters of the invention are shown in FIG. 9. The gene specific primers which target 48986355 (SEQ ID NO:4) were primary primer, 48986355GW (SEQ ID NO:10) and nested primer, 48986355GWnest (SEQ ID NO:11). The adaptor primers used were AP1 (SEQ ID NO:12) and AP2 (SEQ ID NO:13). Using this protocol, several clones were isolated and sequenced.

Figure 10:
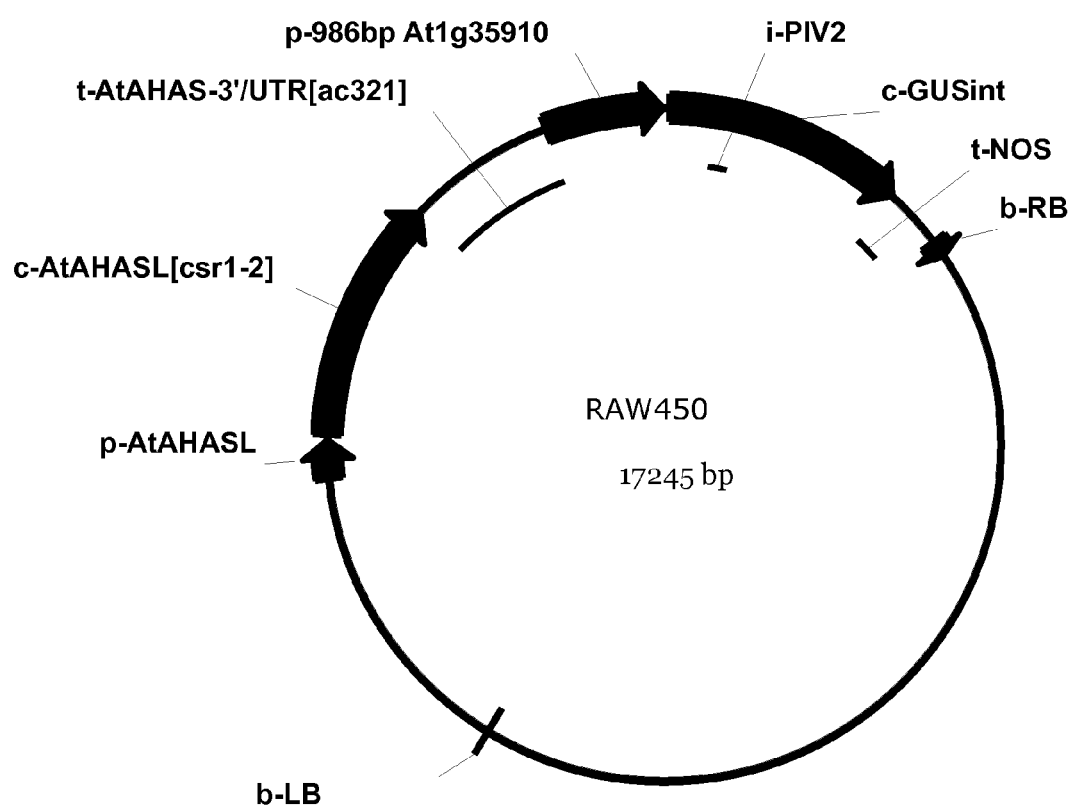
FIG. 10: Map of plasmid RAW450

The longest cloned product was identified as pAW260 (SEQ ID NO:5). A sequence alignment of pAW260 with 48986355 indicated that this clone is identical to 48986355 (SEQ ID NO:4) as shown in FIGS. 10a-c. The alignment revealed that pAW260 contained a 1000 bp promoter sequence upstream of the ATG from nucleotide position of 32 to 1031 of pAW260 sequence (see FIGS. 10a-c). This promoter region was cloned out of pAW260 using standard PCR techniques and the primers 48986355prF (SEQ ID NO: 14) and 48986355prR (SEQ ID NO:15). 48986355prF and 48986355prR amplified the 1000 bp promoter fragment from pAW260 containing the enzyme restriction sites XmaI and AscI respectively for ease of directional cloning. The 48986355 promoter and the 5'UTR sequences, without the restriction sites used for cloning, is shown as SEQ ID NO:3. Nucleotide sequence 1-841 represents the entire promoter sequence with the core promoter region spanning nucleotides 491-841. The TATA signal spans nucleotide 808-814 and the 5' untranslated leader sequence of the mRNA from nucleotides 841-1000.

Example 2

Cloning Trehalose-6-Phosphate Phosphatase (TPP) Promoters from *Arabidopsis*

The *Arabidopsis* At1g35910 and At5g10100 genes were selected based on their similarity to the soybean cDNA sequence indicated in Example 1. *Arabidopsis* (Columbia ecotype) genomic DNA was extracted using the Qiagen DNAeasy Plant Minikit (Qiagen, Valencia, Calif., US). The 1,999 bp (SEQ ID NO:1) and 2,110 bp (SEQ ID NO:2)

genomic DNA regions (putative promoter sequences) directly upstream of the ATG codon including 5'-untranslated region corresponding to *Arabidopsis* trehalose-6-phosphate phosphatase-like genes with locus identifiers, At1g35910 and At5g10100 respectively, were cloned using standard PCR amplification protocols. For this, approximately 0.1 µg of *Arabidopsis* genomic DNA was used as the DNA template in the PCR reaction. The primers used for PCR amplification of the *Arabidopsis* promoter sequences are shown in FIG. 9 and were designed based on the *Arabidopsis* Genomic sequence Database (TAIR). The primer sequences described by SEQ ID NO:6 and SEQ ID NO:8 contain the XmaI restriction site for ease of cloning. The primer sequences described by SEQ ID NO:7 and SEQ ID NO:9 contain the AscI site for ease of cloning. Primer sequences described by SEQ ID NO:6 and SEQ ID NO:7 were used to amplify the promoter region of *Arabidopsis* locus At1g35910. Primer sequences described by SEQ ID NO:8 and SEQ ID NO:9 were used to amplify the promoter region of *Arabidopsis* locus At5g10100.

Amplification reaction mix contained the following: 2.5 µl 10× Hot Start Buffer; 0.15 µl Hot Start Taq DNA polymerase; 0.5 µl 10 mM dNTPs; 0.5 µl 10 µM primer A; 0.5 µl 10 uM primer B; 1.0 µl Columbia *Arabidopsis* genomic DNA (approximately 100 ng); 19.85 µl water. Thermocycler: T3 Thermocycler (Biometra, Goettingen, Germany) was used for the amplification using the following setting: 1 cycle with 900 seconds at 94° C.; 5 cycles with 30 seconds at 94° C., 30 seconds at 52° C., and 120 seconds at 72° C.; 30 cycles with 30 seconds at 94° C., 30 seconds at 62° C., and 120 seconds at 72° C.; 1 cycle with 300 seconds at 72° C.

The amplified DNA fragment size for each PCR product was verified by standard agarose gel electrophoresis and the DNA extracted from gel by Qiagen Gel Extraction Kit (Qiagen, Valencia, Calif., US)). The purified fragments were TOPO cloned into pCR2.1 using the TOPO TA cloning kit following the manufacturer's instructions (Invitrogen). The cloned fragments were sequenced using an Applied Biosystem 373A (Applied Biosystems, Foster City, Calif., US) automated sequencer and verified to be the expected sequence by using the sequence alignment ClustalW (European Bioinformatics Institute, Cambridge, UK) from the sequence analysis tool Vector NTI (Invitrogen, Carlsbad, Calif., USA). The 1,999 bp and 2,110 bp DNA fragments corresponding to the promoter regions of At1g35910 and At5g10100 are shown as SEQ ID NO:1 and SEQ ID NO:2. The restriction sites introduced in the primers for facilitating cloning are not included in the sequences.

Example 3

Binary Vector Construction for Transformation and Generation of Transgenic Hairy Roots To evaluate the expression activity of the cloned promoters, gene fragments corresponding to nucleotides 1-1999 of SEQ ID NO:1, nucleotides 1-2110 of SEQ ID NO:2 and nucleotides 1-1000 of SEQ ID NO:3 were cloned upstream of a GUS reporter gene (bacterial β-glucuronidase or GUS gene (Jefferson (1987) *EMBO J.* 6, 3901-3907) to create the binary vectors pAW284qcz, pAW281qcz, and RAW403, respectively. The plant selectable marker in the binary vectors is a herbicide-resistant form of the acetohydroxy acid synthase (AHAS, EC 4.1.3.18, also known as acetolactate synthase or ALS) gene from *Arabidopsis thaliana* (Sathasivan et al., Plant Phys. 97:1044-50, 1991). ARSENAL (imazapyr, BASF Corp, Florham Park, N.J.) was used as the selection agent.

In the present example, binary vectors pAW284qcz, pAW281 qcz, and RAW403qcz were transformed into *A. rhizogenes* K599 strain by electroporation (Cho et al., (1998) Plant Sci. 138, 53-65). The transformed *Agrobacterium* was used to induce soybean hairy-root formation using the following protocol. Approximately five days before *A. rhizogenes* inoculation, seeds from soybean cultivar Williams 82 (SCN-susceptible) were sterilized with 10% bleach for 10 minutes and germinated on 1% agar at 25° C. with 16-hour/day lighting. Approximately three days before *A. rhizogenes* inoculation, a frozen stock of *A. rhizogenes* Strain K599 containing the binary vector was streaked on LB+kanamycin (50 µg/ml) plates and incubated at 28° C. in darkness. Approximately one day before *A. rhizogenes* inoculation, a colony was picked from the plate and inoculated into liquid LB+kanamycin (50 µg/ml). The culture was shaken at 28° C. for approximately 16 hours. The concentration of *A. rhizogenes* in the liquid culture was adjusted to $OD_{600}=1.0$.

Cotyledons were excised from soybean seedlings and the adaxial side was wounded several times with a scalpel. 15 µl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 µg/ml carbenicillin (to suppress *A. rhizogenes*) and 1 µM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing carbenicillin 500 µg/ml but not ARSENAL.

Example 4

Detection of Promoter Activity in Soybean Hairy Roots

As set forth in Example 3, the promoters of the invention were placed in operative association with the GUS reporter gene to determine their expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction.

To study the promoter activity of SEQ ID NOs:1, 2, and 3 in the presence and absence of nematode infection, several independent transgenic lines were generated from transformation with pAW284qcz, pAW281qcz, and RAW403. Approximately three weeks after subculturing, the transgenic hairy-root lines on MS were inoculated with surface-decontaminated J2 of SCN race 3 at the 2000 J2/plate level. At 12 days after inoculation (DAI), the roots were harvested by removing from the agar plates and gently rinsed with changes in water and stained in GUS staining solution containing X-Gluc (2 mg/l) at 37° C. for 16 hours. At each time point after inoculation, a non-inoculated control plate from each line was also stained in GUS staining solution. After GUS staining, the roots were stained in acid fuchsin and then destained to visualize the nematodes, which were stained red. The roots were then observed under a microscope for detection of GUS expression.

For each transgenic line, 10 randomly picked syncytia were observed and scored for intensity of GUS expression at 12 days after infection (DAI). The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "+" for weak staining, "++" for strong staining. The results for lines transformed with pAW284qcz, pAW281qcz, and RAW403 are presented in FIG. 6.

The result of the GUS staining indicates that for most lines tested, the promoter fragment in pAW284 showed intermediate to strong GUS expression in the syncytia at 12 DAI. In contrast, GUS expression in other root parts such as root tips, vascular tissue, and root cortex was undetected or very weak.

Example 5

Cloning Deletions of At1g35910 (SEQ ID NO:1) Promoter

In order to more accurately define the promoter region of At1g35910 (SEQ ID NO: 1), shorter fragments of the upstream sequence were tested. Plasmid DNA of pAW284qcz was extracted from *E. coli* using the Qiagen Plasmid miniprep kit (Qiagen). The 986 bp and 502 bp promoter deletion fragments of *A. thaliana* locus Atlg35910 promoter (SEQ ID NO:1) contained in pAW284qcz were amplified using standard PCR amplification protocol. For this, approximately 0.1 μg of pAW284qcz plasmid DNA was used as the DNA template in the PCR reaction. The primers used for PCR amplification of the *Arabidopsis* promoter sequences are shown in FIG. 9 and were designed based on the promoter sequence of *A. thaliana* locus At1g35910 promoter (SEQ ID NO:1) contained in pAW284qcz. The primer sequences described by SEQ ID NO:16 and SEQ ID NO:17 contain the PstI restriction site for ease of cloning. The primer sequence described by SEQ ID NO: 18 anneals upstream of the AscI site in pAW284qcz such that an AatII site will be contained in the amplified fragment for ease of cloning. Primer sequences described by SEQ ID NO:16 and SEQ ID NO:18 were used to amplify the 986 bp promoter deletion region of *Arabidopsis* locus Atlg35910 promoter contained in pAW284qcz. Primer sequences described by SEQ ID NO:17 and SEQ ID NO:18 were used to amplify the 502 bp promoter deletion region of *Arabidopsis* locus At1g35910 promoter contained in pAW284qcz.

Amplification reaction mix contained the following: 2.5 μl 10×Pfu Turbo buffer; 0.5 μl Pfu Turbo DNA polymerase; 0.5 μl 10 mM dNTPs; 0.5 μl 10 μM primer A; 0.5 μl 10 μM primer B; 1.0 μl pAW284qcz plasmid DNA (approximately 100 ng); 19.50 μl water. T3 Thermocycler (Biometra, Germany) was used for the amplification using the following setting: 1 cycle with 60 seconds at 94° C.; 32 cycles with 30 seconds at 94° C., 30 seconds at 52° C., and 120 seconds at 72° C.; 1 cycle with 300 seconds at 72° C.

The amplified DNA fragment size for each PCR product was verified by standard agarose gel electrophoresis and the DNA extracted from gel by Qiagen Gel Extraction Kit (Qiagen, Hilden, Germany). The purified fragments were digested with PstI and AatII following the manufacturer's instructions (New England Biolabs, Ipswich, Mass., US). The digested fragments were purified using the Qiagen PCR purification kit (Qiagen). The 986 bp promoter deletion region of At1g35910 promoter amplified using primers SEQ ID NO: 16 and SEQ ID NO: 18 is represented by nucleotides 1014 to 1999 of SEQ ID NO:1. The 502 bp promoter deletion region of At1g35910 promoter amplified using primers SEQ ID NO:17 and SEQ ID NO:18 is represented by nucleotides 1498 to 1999 of SEQ ID NO:1. The restriction sites introduced in the primers for facilitating cloning are not included in the designated sequences.

Example 6

Binary Vector Construction At1g35910 Promoter Deletions for Transformation and Generation of Transgenic Hairy Roots To evaluate the expression activity of the cloned promoter deletions derived from pAW284qcz, gene fragments corresponding to nucleotides 1014 to 1999 of SEQ ID NO:1 and 1498 to 1999 of SEQ ID NO: 1 were cloned upstream of a GUS reporter gene (bacterial β-glucuronidase or GUS gene (Jefferson (1987) *EMBO J.* 6, 3901-3907) to create the binary vectors RAW450 and RAW451, respectively. The plant selection marker in the binary vectors was a mutated AHAS gene from *A. thaliana* that conferred tolerance to the herbicide ARSENAL (imazapyr, BASF Corporation, Florham Park, N.J.).

In the present example, binary vectors RAW450 and RAW451 were transformed into *A. rhizogenes* K599 strain by electroporation. The transformed *Agrobacterium* was used to induce soybean hairy-root formation using the following protocol. Approximately five days before *A. rhizogenes* inoculation, seeds from soybean cultivar Williams 82 (SCN-susceptible) were sterilized with 10% bleach for 10 minutes and germinated on 1% agar at 25° C. with 16-hour/day lighting. Approximately three days before *A. rhizogenes* inoculation, a frozen stock of *A. rhizogenes* Strain K599 containing the binary vector was streaked on LB+kanamycin (50 μg/ml) plates and incubated at 28° C. in darkness. Approximately one day before *A. rhizogenes* inoculation, a colony was picked from the plate and inoculated into liquid LB+kanamycin (50 μg/ml). The culture was shaken at 28° C. for approximately 16 hours. The concentration of *A. rhizogenes* in the liquid culture was adjusted to $OD_{600}=1.0$.

Cotyledons were excised from soybean seedlings and the adaxial side was wounded several times with a scalpel. 15 μl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 μg/ml Carbenicillin (to suppress *A. rhizogenes*) and 1 μM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing Carbenicillin 500 μg/ml but not ARSENAL.

Example 7

Detection of Promoter Deletion Activity in Soybean Hairy Roots

As set forth in Example 6, the promoters of the invention were placed in operative association with the GUS reporter gene to determine their expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction.

To study the promoter activity of the deletion fragments of SEQ ID NO:1 in the presence and absence of nematode infection, several independent transgenic lines were generated from transformation with pAW284qcz, RAW450, and RAW451. Approximately three weeks after subculturing, the transgenic hairy-root lines on MS, were inoculated with surface-decontaminated J2 of SCN race 3 at the 2000 J2/plate level. At 12 days after inoculation (DAI), the roots were harvested by removing from the agar plates and gently rinsed with changes in water and stained in GUS staining solution containing X-Gluc (2 mg/l) at 37° C. for 16 hours. At each time point after inoculation, a non-inoculated control plate from each line was also stained in GUS staining solution. After GUS staining, the roots were stained in acid fuchsin and then destained to visualize the nematodes, which were stained red. The roots were then observed under a microscope for detection of GUS expression.

Figure 7:
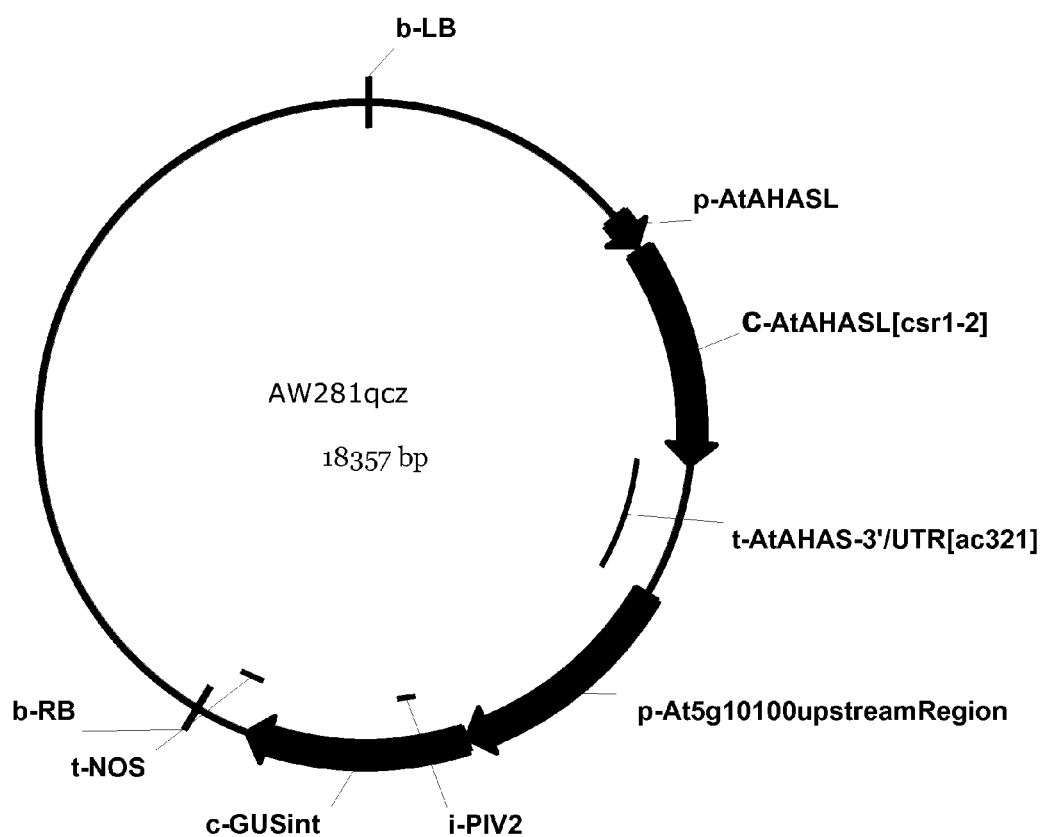
FIG. 7: Map of plasmid AW281qcz

For each transgenic line, 10 randomly picked syncytia were observed and scored for intensity of GUS expression at 12 Days after infection (DAI). The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "+" for weak staining, "++" for strong staining. The results for lines transformed with pAW284qcz, RAW450, and RAW451 are presented in FIG. 7.

The 986 bp promoter sequence contained in RAW450 was not able to confer nematode-induced expression in syncytia. The 502 bp promoter sequence contained in RAW451 was able to confer nematode-induced expression in syncytia, indicating that all of the required regulatory elements are found within the region 502 bp upstream of the start codon. These results are consistent with the results of the promoter analyses using Genomatix set forth in Example 9.

Example 8

PLACE Analysis of Promoters

PLACE (National Institute of Agrobiological Sciences, Ibaraki, Japan) analysis results indicate a TATA box localized at nucleotide position 1871 to nucleotide position 1877 of SEQ ID NO:1 as shown in FIG. 1. In consequence, the 5' untranslated region starts at about nucleotide position 1907. The sequence described by SEQ ID NO:1 ends immediately before the ATG start codon. The potential core region of the promoter described by SEQ ID NO: 1 is from nucleotide position 1557 to nucleotide position 1907.

PLACE analysis results indicate no TATA box localized within about 300 bp of the 3' end of SEQ ID NO:2 as shown in FIG. 2. A predicted 5' untranslated region starts at about nucleotide position 2000. The sequence described by SEQ ID NO:2 ends immediately before the ATG start codon. The potential core region of the promoter described by SEQ ID NO:2 is from nucleotide position 1650 to nucleotide position 2000.

PLACE results indicate a TATA box localized at nucleotide position 808 to nucleotide position 814 of SEQ ID NO:3 as shown in FIG. 3. In consequence, the 5' untranslated region starts at about nucleotide position 841. The potential core region of the promoter described by SEQ ID NO:3 is from nucleotide position 491 to nucleotide position 841.

Example 9

Identification of Promoter Configuration 1, Promoter Configuration 2, and Promoter Configuration 3

Genomatix is a promoter sequence analysis software application containing DiAlign and FrameWorker (Genomatix, Munich, Germany) algorithms. DiAlign is a multiple-sequence alignment tool and FrameWorker can scan a set of DNA sequences for orientation and distance correlated transcription factor binding sites (promoter element classes).

The 3' 650 bp of SEQ ID NO: 1, SEQ ID NO:2, and SEQ ID NO:3 were used for the two Genomatix analyses described above. This corresponds to nucleotides 1349 to 1999 of SEQ ID NO:1, nucleotides 1460 to 2110 of SEQ ID NO:2, and nucleotides 350 to 1000 of SEQ ID NO:3.

Figure 8:
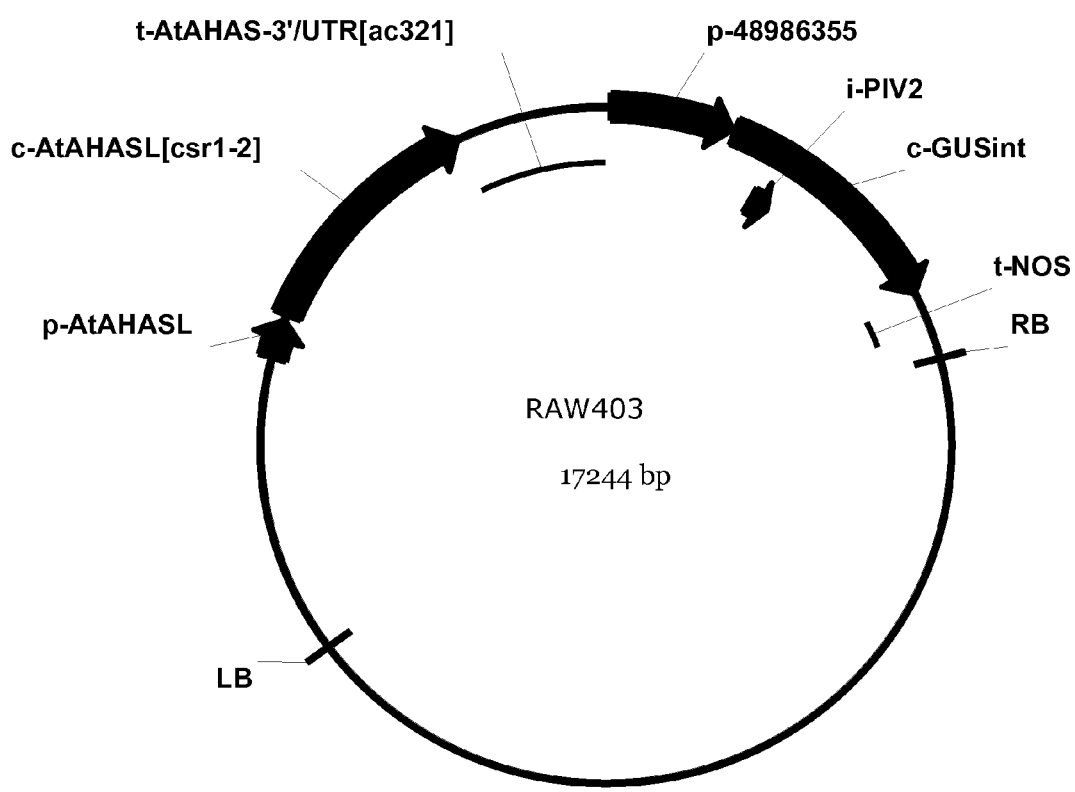
FIG. 8: Map of plasmid RAW403
Figure 11:
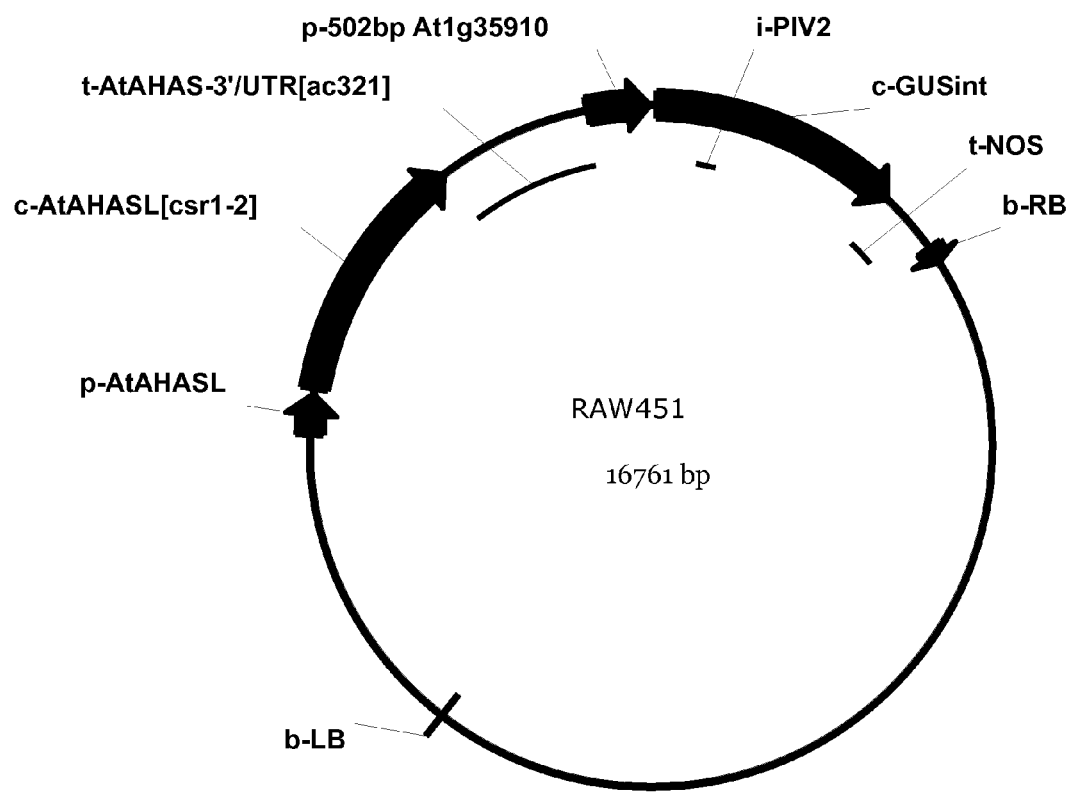
FIG. 11: Map of plasmid RAW451

To determine if there was sequence homology between nucleotides 1349 to 1999 of SEQ ID NO:1, nucleotides 1460 to 2110 of SEQ ID NO:2, and nucleotides 350 to 1000 of SEQ ID NO:3 the Genomatix DiAlign program was used. DiAlign is a (DNA or protein) alignment program that relies on comparison of whole segments of sequences instead of comparison of single nucleic/amino acids. Asterisks (*) indicate the relative degree of local similarity among the input sequences. The maximum possible similarity is represented by 10 '*' signs. The result of this analysis is shown in FIGS. 11a-c. Nucleotides 1349 to 1999 of SEQ ID NO: 1, nucleotides 1460 to 2110 of SEQ ID NO:2, and nucleotides 350 to 1000 of SEQ ID NO:3 were compared using the Genomatix FrameWorker algorithm to determine a common configuration of plant promoter element classes using both known plant promoter elements as well as novel promoter elements associated with soybean cyst nematode inducible promoters identified using the Genomatix CoreSearch algorithm. The parameters used for Genomatix FrameWorker analysis were the following: a distance of 5 to 200 bp between promoter elements, a core similarity of 1.0, and an optimized matrix similarity. Multiple Promoter Configuration models were identified in this analysis. Promoter Configuration 1, Promoter Configuration 2, and Promoter Configuration 3 were generated which comprise 6, 3, and 5 promoter elements, respectively, as summarized in FIG. 8. The model containing six promoter element classes was designated Promoter Configuration 1. Promoter Configuration 1 was determined using a different method than the determination of Promoter Configuration 2 and Promoter Configuration 3. It was discovered that there are multiple common elements between nucleotides 1349 to 1999 of SEQ ID NO:1, nucleotides 1460 to 2110 of SEQ ID NO:2, and nucleotides 350 to 1000 of SEQ ID NO:3. Specifically, there are 3 pairs of elements which occur within close orientation to each other as described in the summary of invention and shown in FIG. 12 for Promoter Configuration 1. The model containing three promoter element classes was designated Promoter Configuration 2. The model containing five promoter element classes was designated Promoter Configuration 3. The locations of promoter element classes contained in the promoter sequences of SEQ ID NO: 1, SEQ ID NO:2, and SEQ ID NO:3 are shown in FIG. 1, FIG. 2, and FIG. 3, respectively. In addition, FIG. 12 shows the common spatial orientation of the promoter element classes in all three Promoter Configurations.

Example 10

Binary Vector Construction to Generate Whole Plant Promoter Constructs with BAR Selection To evaluate the expression activity of the cloned promoter sequences represented by SEQ ID NO:1, SEQ ID NO:2, and SEQ ID NO:3 in soybean nodules after *Bradyrhizobium japonicum* infection and fungal inoculation with *Rhizoctonia solani* form a specialis (f. sp.) glycines and *Fusarium solani* f. sp. glycines, promoter sequences represented by SEQ ID NO:1, SEQ ID NO:2, and SEQ ID NO:3 were cloned upstream of a GUS reporter gene to create the binary vectors RAW425, RAW424, and RTJ131, respectively. The plant selection marker in the binary vectors is a BAR gene driven by the constitutive nopaline synthase gene promoter (p-NOS, An G. at al., The Plant Cell 3:225-233, 1990). Binary vectors RAW425, RAW424, and RTJ131 were used to generate transgenic roots for analysis.

Example 11

Soybean Rooted Plant Assay System

Clean soybean seeds from soybean cultivar *Glycine max* cv. Williams 82 were sterilized in a chamber with a chlorine gas produced by adding 3.5 ml 12NHCl drop wise into 100 ml bleach. All operations were conducted in a fume hood. After 24 hours in the chamber, seeds were removed and used immediately or stored at room temperature until use. Discolored seeds or cracked seeds were removed. To imbibe seeds, warm GM medium was poured around seeds until the seeds were entirely covered by the medium. Seedlings were grown in the light for 5-7 days until the epicotyl was extended beyond the cotyledons. Seedlings can be stored at 4° C. overnight before being used in transformation. The GM (Germination Medium) comprises: 1×B5 salts and vitamins, 1×MS iron stock, 2% sucrose, and 0.8% Noble agar at pH 5.8. As an alternative, soybean seeds can be germinated in 1% agar (50 ml) in Petri dishes for 7 days before *Agrobacterium* inoculation.

Three days before *Agrobacterium* inoculation, an *Agrobacterium* culture, for example, the disarmed *A. rhizogenes* strain K599 liquid culture, was placed in 5 ml LB+Kan50 (containing 50 ug/ml Kanamycin) media in a 28° C. shaker overnight. The next day, 1 ml of the culture was taken and spread onto an LB+Kan50 agar plate. The plates were incubated in a 28° C. incubator for two days. At the end of the two-day period the plates were covered with thick colonies. One plate was prepared for every 50 explants to be inoculated.

Soybean seedlings prepared as described above had elongated hypocotyls approximately 3 to 5 cm in length with visible epicotyls. The explants were then prepared by removing the epicotyls and part of the hypocotyls. The explant contained one or two cotyledons, an axillary meristem and the hypocotyl about 2-3 cm in length. The seed coat was removed to facilitate cotyledon development. The cut end of the hypocotyl was the target for transformation/infection.

Alternatively, cotyledons containing the proximal end from its connection with the seedlings were used as another type of explant for transformation. The cut end was the target for *Agrobacterium* inoculation.

After the explants were cut off the seedlings, the cut end was immediately dipped onto the thick *A. rhizogenes* colonies prepared above so that the colonies were visible on the cut end. The explants were placed onto 1% agar in Petri dishes for co-cultivation. Approximately 10 explants were placed in one dish. The dishes were sealed with Saran wrap and co-cultured at 25-27° C. under light for 6 days.

After the transformation and co-cultivation step in Example 15, soybean explants were transferred to rooting induction medium with a selection agent, for example, S-B5-605 for Bar gene selection, or S-B5-708 for an AHAS gene selection. The explants were inserted so that the callus at the bottom was just below the medium surface. Six to nine explants were placed in each Petri dish. Cultures were maintained in the same condition as in the co-cultivation step.

The S-B5-605 medium comprises: 0.5×B5 salts, 3 mM MES, 2% sucrose, 1× B5 vitamins, 400 µg/ml Timentin, 0.8% Noble agar, and 3 µg/ml Glufosinate Ammonion (selection agent for Bar gene) at pH 5.8. The S-B5-708 medium comprises: 0.5× B5 salts, 3 mM MES, 2% sucrose, 1× B5 vitamins, 400 µg/ml Timentin, 0.8% Noble agar, and 1 µM Imazapyr (selection agent for AHAS gene) at pH5.8.

Two to three weeks after the root induction, transformed roots were formed on the cut ends of the explants. Elongated roots located on the tissues above the callus were removed during the transfer. For bar gene selection, explants were transferred to root elongation medium supplemented with 3 mg/l Glufosinate Ammonion and 400 mg/l Timentin without IBA (S-MS-607 medium) for further selection. For AHAS gene selection, explants were transferred to the same selection medium (S-B5-708 medium) for further selection. Transgenic roots proliferated well within one week in the medium and were ready to be subcultured. The S-MS-607 medium comprises: 0.2×MS salts and B5 vitamins, 2% sucrose, 400 mg/l Timentin, and 3 mg/L Glufosinate Ammonion at pH5.8

Strong and white soybean roots were excised from the rooted explants and cultured in root growth medium supplemented with 200 mg/l Timentin (S-MS-606 medium) in either six-well plates or Petri plates. The main root tips were removed to induce secondary root growth. Cultures were maintained at room temperature under the dark condition. Each root event was subcultured into three different wells as replicates. Subcultured roots in each well would vigorously grow lateral roots. The S-MS-606 medium comprises: 0.2× MS salts and B5 vitamins, 2% sucrose, and 200 mg/l timentin at pH5.8.

Example 12

Rooted Plant Assay System Nodule Induction and Detection of Promoter Activity in Nodules As set forth in Example 10, the promoter polynucleotides of the invention were placed in operative association with the GUS reporter gene to determine expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction.

In the present example, binary vectors RAW425, RAW424, and RTJ131 were transformed into the disarmed *A. rhizogenes* K599 strain SHA017 (pSB1) by electroporation. The transformed *Agrobacterium* was used to induce soybean TRAP root formation using the protocol outlined in Examples 11, 12, 13, 15, 16, and 17. Rooted explants were removed from the elongation media and the roots were washed with water to remove excess media. The entire explants were transferred to 4 inch pots containing wet sand. The explants were watered every 2 days with Buffered Nodulation Medium (Ehrhardt et al., 1992). After two days in wet sand, the explant roots were inoculated with *Bradyrhizobium japonicum.*

For this, a 4 ml *Bradyrhizobium japonicum* culture was started in YM liquid media and grown at 28 C with shaking. YM media contains per liter: 10 g Mannitol, 0.4 g yeast extract, 1 ml K2HPO₄ (10% w/v stock), 4 ml KH2PO4 (10% w/v stock), 1 ml NaCl (10% w/v stock), and 2 ml MgSO4.7H20 (10% w/v stock). The pH was adjusted to 6.8 and the 1 liter final volume solution was autoclaved. After 7 days, 600 microliters of the starter culture was transferred to 40 ml of fresh YM liquid media. Multiple 40 ml cultures were started. The cultures grew for 48 hours at 28 C with shaking to an OD600 of approximately 0.2. The *Bradyrhizobium japonicum* cultures were combined and diluted 6 fold with Buffered Nodulation Medium. Each pot containing a rooted-explant was inoculated with approximately 25 ml of the diluted *Bradyrhizobium japonicum* culture. Approximately 4 holes about 2 inches deep were created in the sand using a wooden dowel and the diluted *Bradyrhizobium japonicum* culture was inoculated into the holes using a pipette. Beginning the day after inoculation, the rooted explants were watered with Buffered Nodulation Medium every 2 days.

After 2 weeks, the rooted plant assay systems were removed from the 4 inch pots and the roots were washed with water to remove sand. Regions of root containing nodules were dissected using a razor blade and placed into GUS staining solution containing X-Gluc (2 mg/l) and then transferred to 37° C. for 16 hours. Some nodules were sliced in half using a razor blade. The GUS staining solution was removed and replaced with a solution containing equal parts of glycerol, water, and acetic acid. The root nodules were then observed for GUS staining. It was observed that the promoter described by SEQ ID NO: 1 contained in construct RAW425 did induce GUS expression in root nodules. It was observed that the promoter described by SEQ ID NO:2 contained in RAW424 did induce GUS expression in root nodules. It was observed that the promoter described by SEQ ID NO:3 contained in construct RTJ131 did induce GUS expression in root nodules.

Example 13

Whole Plant GUS Staining

Transgenic soybean whole plants are generated containing the promoter sequences represented by SEQ ID NO:1, SEQ ID NO:2, and SEQ ID NO:3 in operative association with the GUS reporter gene by transforming constructs RAW425, RAW424, and RTJ131, respectively, to characterize promoter expression in response to nematode infection in roots and whole plant tissues throughout the plant life cycle. Representative methods of promoter characterization in soybean whole plants include but are not limited to the following descriptions. Transgenic soybean T1 seeds are tested for zygosity and single copy events are germinated, grown in greenhouse conditions, and sampled for GUS expression at various stages of development in leaf, stem, flower, embryo, and seed pod tissues. In addition, root tissues are harvested at various times before and after SCN infection in inoculated and un-inoculated control roots. Multiple plants are tested for each event to determine consistent trends in the GUS staining analysis. Harvested samples are cut off of the plant and immediately placed into GUS staining solution containing X-Gluc (2 mg/l), vacuum infiltrated for 20 minutes, and transferred to 37° C. for 16 hours. The tissues are then observed and scored for the intensity of GUS staining.

What is claimed is:

1. An expression cassette comprising an isolated promoter polynucleotide selected from the group consisting of:
   a) a polynucleotide comprising nucleotides 1 to 1999 of SEQ ID NO:1;
   b) a polynucleotide comprising nucleotides 1557 to 1907 of SEQ ID NO:1;
   c) a polynucleotide comprising nucleotides 1498 to 1999 of SEQ ID NO:1; and
   d) a polynucleotide comprising nucleotides 1349 to 1999 of SEQ ID NO:1 said isolated promoter polynucleotide being operably linked to a second heterologous polynucleotide.

2. The expression cassette of claim 1, wherein the second heterologous polynucleotide is selected from the group consisting of an open reading frame, a portion of an open reading frame, a polynucleotide encoding a fusion protein, an antisense polynucleotide, a polynucleotide encoding a double-stranded RNA construct, and a transgene.

3. The expression cassette of claim 2, wherein said second heterologous polynucleotide confers to a plant a trait or property selected from the group consisting of increased yield, increased resistance under stress conditions, increased nutritional quality, increased resistance to pathogens, and increased or modified protein or oil content of a plant.

4. A transgenic plant transformed with an expression cassette comprising an isolated promoter polynucleotide capable of mediating root-preferred or pathogen-inducible expression, said promoter polynucleotide being selected from the group consisting of:
   a) a polynucleotide comprising nucleotides 1 to 1999 of SEQ ID NO: 1; and
   b) a polynucleotide comprising nucleotides 1557 to 1907 of SEQ ID NO:1, or nucleotides 1498 to 1999 of SEQ ID NO:1, or nucleotides 1349 to 1999 of SEQ ID NO:1
wherein the expression cassette further comprises a second heterologous polynucleotide operably linked to the promoter polynucleotide.

5. The plant of claim 4, wherein the plant is selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, eggplant, pepper, oilseed rape, canola, beet, cabbage, cauliflower, broccoli, lettuce, *Lotus* sp., *Medicago trunculata*, perennial grass, ryegrass, and *Arabidopsis thaliana*.

6. A method of producing a transgenic plant, wherein the method comprises the steps of:
   a) preparing a construct comprising an isolated promoter selected from the group consisting of:
      (i) a polynucleotide comprising nucleotides 1 to 1999 of SEQ ID NO:1;
      (ii) a polynucleotide comprising nucleotides 1557 to 1907 of SEQ ID NO:1;
      (iii) a polynucleotide comprising nucleotides 1498 to 1999 of SEQ ID NO:1; and
      (iv) a polynucleotide comprising nucleotides 1349 to 1999 of SEQ ID NO:1
   wherein the promoter is operably linked to a second heterologous polynucleotide;
   b) transforming a plant cell with the construct of a) wherein the promoter induces root-preferred transcription or induces transcription of the operably linked second heterologous polynucleotide in the plant cell in response to a pathogen stimulus; and
   c) regenerating the transformed plant cell to produce a transgenic plant having pathogen resistance or improved pathogen resistance.

7. The method of claim 6, wherein the second heterologous polynucleotide confers to the plant a trait or property selected from the group consisting of increased yield, increased resistance under stress conditions, increased nutritional quality, increased resistance to nematodes, and increased or modified protein or oil content of a plant.

* * * * *